(12) United States Patent
Masliah et al.

(10) Patent No.: US 8,846,682 B2
(45) Date of Patent: Sep. 30, 2014

(54) COMPOUND SUITABLE FOR THE TREATMENT OF SYNUCLEOPATHIES

(75) Inventors: Eliezer Masliah, San Diego, CA (US); Edward M. Rockenstein, Chula Vista, CA (US); Wolfgang Wrasidlo, La Jolla, CA (US); Igor Flint Tsigelny, San Diego, CA (US)

(73) Assignee: Neuropore Therapies, Inc., San Diego, CA (US)

( * ) Notice: Subject to any disclaimer, the term of this patent is extended or adjusted under 35 U.S.C. 154(b) by 0 days.

(21) Appl. No.: 13/516,543

(22) PCT Filed: Dec. 16, 2010

(86) PCT No.: PCT/US2010/060862
§ 371 (c)(1),
(2), (4) Date: Aug. 28, 2012

(87) PCT Pub. No.: WO2011/084642
PCT Pub. Date: Jul. 14, 2011

(65) Prior Publication Data
US 2013/0035342 A1    Feb. 7, 2013

Related U.S. Application Data

(60) Provisional application No. 61/287,082, filed on Dec. 16, 2009.

(51) Int. Cl.
| | | |
|---|---|---|
| *A61K 31/496* | (2006.01) |
| *A61K 31/52* | (2006.01) |
| *A61K 31/454* | (2006.01) |
| *A61K 31/519* | (2006.01) |
| *A61P 25/00* | (2006.01) |
| *A61P 25/16* | (2006.01) |
| *A61P 25/28* | (2006.01) |
| *C07D 403/14* | (2006.01) |
| *C07D 473/00* | (2006.01) |
| *C07D 487/04* | (2006.01) |
| *C07D 417/14* | (2006.01) |
| *C07D 401/14* | (2006.01) |
| *C07D 403/12* | (2006.01) |
| *C07D 417/12* | (2006.01) |
| *C07D 413/12* | (2006.01) |

(52) U.S. Cl.
CPC ............ *C07D 473/00* (2013.01); *C07D 487/04* (2013.01); *C07D 403/12* (2013.01); *C07D 417/12* (2013.01); *C07D 413/12* (2013.01)
USPC ............ 514/252.16; 514/254.02; 514/254.05; 514/322; 544/369; 544/366; 544/277; 546/199

(58) Field of Classification Search
USPC .................. 514/252.16, 254.02, 254.05, 322; 544/369, 366, 277, 280; 546/199
See application file for complete search history.

(56) References Cited

U.S. PATENT DOCUMENTS

| | | |
|---|---|---|
| 5,591,695 A | 1/1997 | Newton |
| 6,096,688 A | 8/2000 | Newton et al. |
| 2009/0054410 A1 | 2/2009 | Griffioen et al. |

FOREIGN PATENT DOCUMENTS

| | | |
|---|---|---|
| DE | 102004051277 A1 | 4/2006 |
| EP | 0726263 A2 | 8/1996 |
| WO | 98/27108 A2 | 6/1998 |
| WO | 2005/074642 A2 | 8/2005 |
| WO | 2010/142801 A1 | 12/2010 |

OTHER PUBLICATIONS

Appell (Antagonist that Demonstrate Species Differences in Neurokinin-1 Receptors, the American Society for Phamacology and Experimental Therapeutics, 1992, pp. 772-778).*
International Search Report for International Application No. PCT/US2010/060862, European Patent Office, Apr. 20, 2011.
Database Registry, Chemical Abstracts Service, Accession No. 1193140-75-8, Nov. 22, 2009.

* cited by examiner

*Primary Examiner* — San-Ming Hui
*Assistant Examiner* — Kathrien Cruz
(74) *Attorney, Agent, or Firm* — Morrison & Foerster LLP

(57) ABSTRACT

The present invention relates to a compound of formula (I): Wherein $R_1$ is a substituted or unsubstituted aromatic hetero- or homocyclic or a substituted or unsubstituted alicyclic hetero- or homocyclic group; $R_2$ is an alkyl group with 1 to 18 carbon atoms or a substituted or unsubstituted cycloalkyl or aryl group; $R_3$ is a substituted or unsubstituted aromatic hetero- or homocyclic or a substituted or unsubstituted alicyclic hetero- or homocyclic group; L is a single bond, an alkyl group having 1 to 6 carbon atoms, NHCO, O, S, NHCONH or NHCOO; X, Y and Z are independently O, N, NH, S or CH; W is a single bond or an alkyl group having from 1 to 6 carbon atoms; or a pharmaceutically acceptable salt thereof or a pharmaceutically acceptable solvate of said compound or salt.

3 Claims, 14 Drawing Sheets

R1 = hydrophilic aromatic or heterocyclic group
R2 = aliphatic hydrocarbon or alicyclic hydrophobic group or nil
R3 = aliphatic or alicyclic group with basic character
X = NH, O, S, CH2
Y = C=O, C=S, C=NH
Z = CH, O, S, -N-, NH
L = CH2, CO2, CH2-S, CH2-SO. CH2-SO2, O, S, C=O or nil Example:

Figure 3 cont.

*N*-(1-(1*H*-benzo[d]imidazol-2-yl)-2-propoxyethyl)-1-(2-(dimethylamino)ethyl)-2,5-dioxo-2,5-dihydro-1*H*-pyrrole-3-carboxamide Chemical Formula: $C_{21}H_{27}N_5O_4$
Exact Mass: 413.21
Molecular Weight: 413.47
m/z: 413.21 (100.0%), 414.21 (23.2%), 415.21 (3.7%), 414.20 (1.8%)
Elemental Analysis: C, 61.00; H, 6.58; N, 16.94; O, 15.48

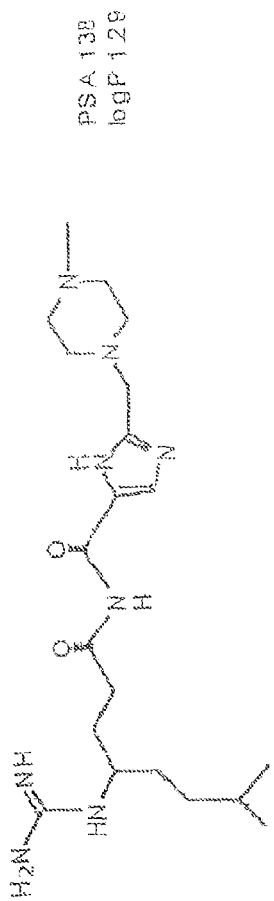

*N*-(4-guanidino-7-methyloctanoyl)-2-((4-methylpiperazin-1-yl)methyl)-1*H*-indazole-5-carboxamide PSA 138
logP 1.29

Chemical Formula: $C_{64}H_{91}N_{17}O_{10}$
Exact Mass: 1257.71
Molecular Weight: 1258.52
m/z: 1257.71 (100.0%), 1258.72 (70.6%), 1259.72 (26.7%), 1260.72 (8.4%), 1258.71 (6.3%), 1259.71 (4.6%)
Elemental Analysis: C, 61.08; H, 7.29; N, 18.92; O, 12.71

(E)

(J)

COMPOUND SUITABLE FOR THE TREATMENT OF SYNUCLEOPATHIES

CROSS REFERENCE TO RELATED APPLICATIONS

This application is the U.S. National Stage of International Application No.: PCT/US2010/060862, filed Dec. 16, 2010, which claims the benefit of U.S. Provisional Application No. 61/287,082, filed Dec. 16, 2009.

The present invention relates to compounds suited to be used to treat and/or prevent synucleopathies.

Protein misfolding and aggregation into toxic oligomers has been linked with the neurodegenerative process in Alzheimer's Disease (AD), Parkinson's Disease (PD) and other age-associated neurological disorders. Together, AD and PD affect over 10 million people in the US and Europe alone. In PD and related conditions such as Dementia with Lewy bodies (DLB), Parkinson's Disease Dementia (PDD), Multiple System Atrophy (MSA) the damage of nerve terminals has been linked to abnormal accumulation of alpha-synuclein (SYN), a synaptic protein that under physiological conditions is involved in synaptic vesicle recruitment and plasticity. Jointly, PD, PDD and DLB are denominated Lewy body disease (LBD). In patients with PD motor deficits have been linked to the degeneration of dopaminergic neurons. However, patients with PD also develop non-motor symptoms such as memory and olfactory deficits that result from the degeneration of other neuronal populations in the CNS.

Previous studies have considered SYN as an unstructured molecule, however studies in biological membranes and molecular dynamics studies over prolonged periods of time have shown that SYN can adopt complex structures with two-alpha helixes at the N-terminus and a movable C-terminus tail. Based on these studies, it was recently discovered that SYN could form propagating and non-propagating dimers. The propagating dimers arrange in a tail to tail conformation (N-term of one SYN with the N-term of the other SYN) that allows for the incorporation of additional SYN molecules. The non-propagating dimers (N-term of one SYN with the C-term of the other SYN) arrange in a head to tail orientation and do not allow further aggregation. Molecular dynamics simulations and in vitro studies demonstrated that propagating dimers might constitute the nidus for the formation of toxic oligomers (pentamers, hexamers, heptamers) that are centrally involved in the pathogenesis of PD and related conditions.

Most compounds currently under testing for PD are designed to improve dopaminergic neurotransmission. A few new experimental compounds have been developed to target SYN aggregation by blocking fibril formation rather than oligomers. The role of fibril formation in PD is controversial and most recent studies consider that fibrilization might play a role at isolating more toxic oligomers.

A number of relatively specific and non-specific SYN inhibitors are currently under development. Most of these molecules such as curcumin, rifampicin and flavinoids display anti-oxidant properties. However, none of the compounds known specifically target SYN arrays involved in the formation of toxic oligomers.

It is an object of the present invention to provide compounds which specifically block the formation of propagating dimers and toxic SYN oligomers. Consequently, these compounds can be used to treat individuals suffering from synucleopathies, slow down the progress and prevent the outbreak of said diseases.

The present invention relates to a compound of formula (I):

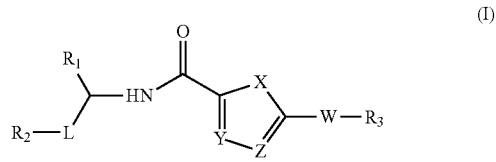

wherein
$R_1$ is a substituted or unsubstituted aromatic hetero- or homocyclic or a substituted or unsubstituted alicyclic hetero- or homocyclic group,
$R_2$ is an alkyl group with 1 to 18 carbon atoms or a substituted or unsubstituted cycloalkyl or aryl group,
$R_3$ is a substituted or unsubstituted aromatic hetero- or homocyclic or a substituted or unsubstituted alicyclic hetero- or homocyclic group,
L is a single bond, an alkyl group having 1 to 6, preferably 1 to 5, more preferably 1 to 4, even more preferably 1 to 3, carbon atoms, NHCO, O, S, NHCONH or NHCOO,
X, Y and Z are independently O, N, NH, S or CH,
W is a single bond or an alkyl group having from 1 to 6 carbon atoms,
or a pharmaceutically acceptable salt thereof or a pharmaceutically acceptable solvate of said compound or salt.

It turned out that the organic heteroaromatic compounds according to the present invention having formula (I) specifically block the formation propagating dimers and toxic SYN oligomers. These compounds bind selectively misfolded SYN and prevent aggregation of oligomers into toxic species. These compounds consequently block the formation of propagating dimers.

It was found that organic compounds in the molecular weight range from 150 to 600, preferably 200 to 500, having a central heteroaromatic ring structure linked to three different types of moieties $R_1$, $R_2$ and $R_3$ shown in the general formula above, are suitable to block SYN aggregation. The central scaffold of the compound according to formula (I) is composed of —NH—CO— and a heteroaromatic ring structure. This scaffold is linked via linkage moieties designated as L and W to $R_1$, $R_2$ and $R_3$ (formula I). $R_1$, $R_2$ and $R_3$ are diversity inputs for affecting the affinity of the compound to the SYN target. $R_1$ is a substituted or unsubstituted aromatic hetero- or homocyclic or a substituted or unsubstituted alicyclic hetero- or homocyclic group. $R_1$ is preferably a substituted or unsubstituted aromatic or heterocyclic group, preferably a fused heteroaromatic ring incorporating at least one basic nitrogen atom, $R_2$ is preferably either a linear aliphatic moiety or a short chain aliphatic moiety connected to a alicyclic ring structure. It is noted that substituent $R_2$ of formula (I) is hydrophobic. This property of $R_2$ is important for the biological activity of the compounds of the present invention. $R_3$ is a substituted or unsubstituted aromatic hetero- or homocyclic or a substituted or unsubstituted alicyclic hetero- or homocyclic group. $R_3$ is preferably composed of a linear alicyclic or linear chain structure with basic character including basic nitrogen atoms.

The central scaffold composed of a heterocyclic 5-membered ring of a variety of structures including triazoles, imidazoles, imides, oxazoles, thiazoles and any combination of heteroatoms independently having nitrogen, oxygen or sulfur atoms in the rings. The linker fragment L can be either a hydrocarbon chain, an ester group, a thioether, methylene sulfoxide, methylene sulfone or a simple oxygen, sulfur or carbonyl bridge, preferably NHCO, O, S, NHCONH or NHCOO. Linker W can be nil (i.e. single bond), resulting in a compound lacking substituent $R_3$ or being bound directly to a carbon atom of the heterocyclic 5-membered ring according to formula (I), or an alkyl group comprising or consisting of 1 to 6 or 1 to 15, preferably 1 to 10, more preferably 1 to 8, even more preferably 1 to 5 carbon atoms.

The heteroaromatic compounds described herein are designed to bind to pathological forms of SYN, which based on previous studies are usually located in the membranes. In contrast the physiological SYN is usually found in the cytoplasmic fraction. This shows that the compounds of the present invention have access to the abnormal SYN, while the native molecule is affected by said compounds.

Substituents $R_1$ and $R_3$ may be identical or different.

According to a particularly preferred embodiment of the present invention substituent L is NHCONH. It turned out that a compound of formula (I) or (Ia) having an urea group at this position is more stable than compounds wherein L is another substituent.

The term "pharmaceutically acceptable salt", as used herein, relates to salts which are toxicologically safe for human and animal administration. For example, suitable pharmaceutically acceptable salts include, but are not limited to, salts of pharmaceutically acceptable inorganic acids such as hydrochloric, sulphuric, phosphoric, nitric, carbonic, boric and sulfamic acids, or salts of pharmaceutically acceptable organic acids such as acetic, propionic, butyric, tartaric, hydroxymaleic, fumaric, maleic, citric, lactic, gluconic, benzoic, succinic, methanesulphonic, α-alic, phenylacetic, toluenesulphonic, benzenesulphonic, salicyclic, sulphanilic, aspartic, glutamic, edelic, stearic, palmitic, oleic, lauric, pantothenic, tannic, ascorbic and valeric acids.

An alternative aspect of the present invention relates to a compound of formula (Ia):

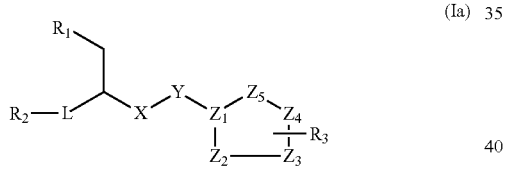

(Ia)

wherein $R_1$ is a hydrophilic aromatic or heterocyclic group, $R_2$ is an aliphatic hydrocarbon or alicyclic hydrophobic group or nil, $R_3$ is an aliphatic or alicyclic group with basic character, X is NH, O, S, or $CH_2$, Y is C=O, C=S or C=NH, Z is independently CH, C=O, O, S, —N— or NH, and L is $CH_2$, $CO_2$, $CH_2$—S, $CH_2$—SO, $CH_2$—$SO_2$, O, S or C=O, or nil, or a pharmaceutically acceptable salt thereof or a pharmaceutically acceptable solvate of said compound or salt.

$Z_1$ of formula (Ia) may be C or N, $Z_2$ may be C, N, C=O or NH, $Z_3$ may be C=O, N or C, $Z_4$ may be C and $Z_5$ may be N, S, NH, O, C=O or S.

$R_1$, $R_2$ and $R_3$ of formula (Ia) are preferably hydrophilic aromatic or heterocyclic groups, aliphatic hydrocarbon or alicyclic hydrophobic groups or aliphatic or alicyclic groups with basic character, respectively.

According to a preferred embodiment of the present invention $R_1$ of formula (I) is selected from the group consisting of a phenyl, naphyl, pyridinyl, pyrimidinyl, quinolinyl, benzothienyl, indolyl, pyrazinyl, isoindolyl, isoquinolinyl, quinazolinyl, imidazolinyl, benzofuranyl, thienyl, pyrrolyl and thiazolyl group, or a substituted heteroring structure comprising alkoxy substituents or halo substituents selected from the group consisting of fluoro, chloro, bromo or iodo groups.

According to a further preferred embodiment of the present invention $R_2$ of formula (I) is a substituted or unsubstituted cycloalkyl group selected from the group consisting of cyclopropyl, cyclobutyl, cyclopentyl, cylohexyl, cyclopeptyl and cyclooctyl, or a substituted or unsubstituted aryl group selected from the group consisting of phenyl, alkoxyphenyl and halide substituted phenyl groups, said halide substituted phenyl groups comprising fluoro, chloro, bromo or iodo groups.

According to a preferred embodiment of the present invention $R_3$ of formula (I) is selected from the group consisting of piperadine, piperazine, moppholino, sthiomorpholine, imidiazolo, pyrrolidonyl, pyrolyl, pyrazolyl, imidazolyl, imidazolidinyl and substituted N-substituted piperazine comprising methyl, ethyl, propyl, butyl, pentyl, hexanyl, heptyl or octyl substituents.

According to a particularly preferred embodiment of the present invention $R_1$ is a bicyclic heteroaromatic group, preferably selected from the group consisting of

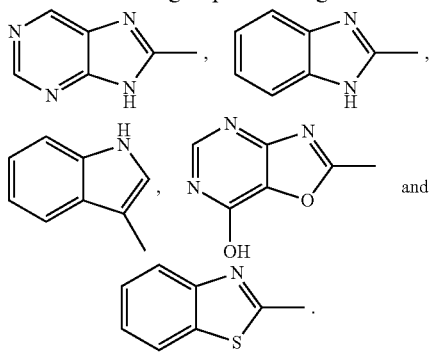

and

According to a preferred embodiment of the present invention $R_2$ is an alkyl group with 1 to 15, preferably 1 to 10, more preferably 1 to 8, even more preferably 1 to 5, carbon atoms.

According to a further preferred embodiment of the present invention $R_2$ is selected from the group consisting of

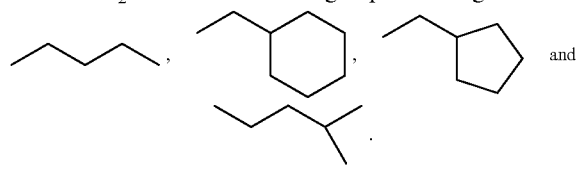

and $R_3$ is preferably a hetero-alicyclic group preferably selected from the group consisting of

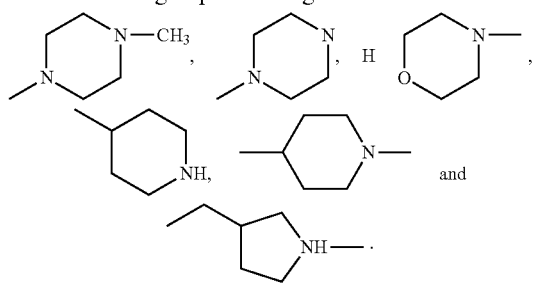

and

According to a preferred embodiment of the present invention

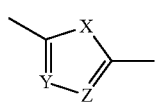

is preferably selected from the group consisting of

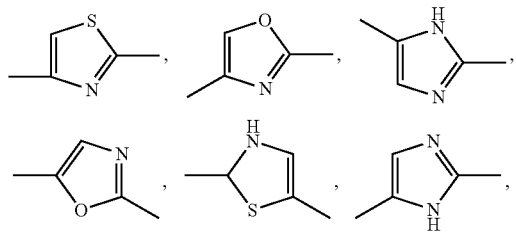

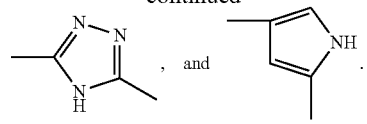

According to a particularly preferred embodiment of the present invention the compounds of the present invention having general structure of formula (I) have the following substituents:

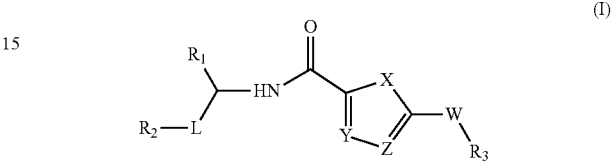

TABLE A

| No. | R1 | R2 | R3 | L | W | X | Y | Z |
|---|---|---|---|---|---|---|---|---|
| 1 | 3-indolylmethyl | n-butyl | 4-methylpiperazinyl | NHCONH | — | S | CH | N |
| 2 | 3-indolylmethyl | n-butyl | 4-methylpiperazinyl | NHCO | — | S | CH | N |
| 3 | 3-indolylmethyl | n-butyl | 4-methylpiperazinyl | NHCOO | — | S | CH | N |
| 4 | 3-indolylmethyl | n-butyl | 4-methylpiperazinyl | NHCO | — | S | N | CH |
| 5 | 3-indolylmethyl | n-butyl | 4-methylpiperazinyl | NHCO | — | NH | N | N |
| 6 | 3-indolylmethyl | n-butyl | 4-methylpiperazinyl | NHCONH | — | S | N | CH |
| 7 | 3-indolylmethyl | n-butyl | 4-methylpiperazinyl | NHCONH | — | NH | N | N |

TABLE A-continued

| No. | R1 | R2 | R3 | L | W | X | Y | Z |
|---|---|---|---|---|---|---|---|---|
| 8 | purine | pentyl | N-methylpiperazine | NHCONH | — | S | CH | N |
| 9 | purine | pentyl | N-methylpiperazine | NHCO | — | S | CH | N |
| 10 | purine | pentyl | N-methylpiperazine | NHCOO | — | S | CH | N |
| 11 | purine | pentyl | N-methylpiperazine | NHCO | — | S | N | CH |
| 12 | purine | pentyl | N-methylpiperazine | NHCO | — | NH | N | N |
| 13 | purine | pentyl | N-methylpiperazine | NHCONH | — | S | N | CH |
| 14 | purine | pentyl | N-methylpiperazine | NHCONH | — | NH | N | N |
| 15 | indole | pentyl | 4-methylpiperazine | NHCONH | — | S | CH | N |
| 16 | indole | pentyl | 4-methylpiperazine | NHCO | — | S | CH | N |
| 17 | indole | pentyl | 4-methylpiperazine | NHCOO | — | S | CH | N |
| 18 | indole | pentyl | 4-methylpiperazine | NHCO | — | S | N | CH |
| 19 | indole | pentyl | 4-methylpiperazine | NHCO | — | NH | N | N |

TABLE A-continued

| No. | R1 | R2 | R3 | L | W | X | Y | Z |
|---|---|---|---|---|---|---|---|---|
| 20 | 3-methylindole | pentyl | 4-methylpiperazin-1-yl (N-CH₃) | NHCONH | — | S | N | CH |
| 21 | 3-methylindole | pentyl | 4-methylpiperazin-1-yl | NHCONH | — | NH | N | N |
| 22 | 8-methyl-9H-purine | pentyl | 4-methylpiperazin-1-yl | NHCONH | — | S | CH | N |
| 23 | 8-methyl-9H-purine | pentyl | 4-methylpiperazin-1-yl | NHCO | — | S | CH | N |
| 24 | 8-methyl-9H-purine | pentyl | 4-methylpiperazin-1-yl | NHCOO | — | S | CH | N |
| 25 | 8-methyl-9H-purine | pentyl | 4-methylpiperazin-1-yl | NHCO | — | S | N | CH |
| 26 | 8-methyl-9H-purine | pentyl | 4-methylpiperazin-1-yl | NHCO | — | NH | N | N |
| 27 | 8-methyl-9H-purine | pentyl | 4-methylpiperazin-1-yl | NHCONH | — | S | N | CH |
| 28 | 8-methyl-9H-purine | pentyl | 4-methylpiperazin-1-yl | NHCONH | — | NH | N | N |
| 29 | 3-methylindole | isopentyl | 4-methylpiperazin-1-yl (NH) | NHCONH | — | S | CH | N |
| 30 | 3-methylindole | isopentyl | 4-methylpiperazin-1-yl (NH) | NHCO | — | S | CH | N |

TABLE A-continued
| No. | R1 | R2 | R3 | L | W | X | Y | Z |
|-----|----|----|----|----|----|----|----|----|
| 31 | 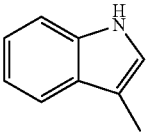 | 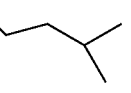 | 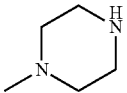 | NHCOO | — | S | CH | N |
| 32 | 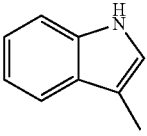 | 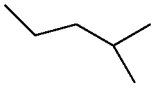 | 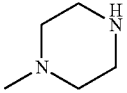 | NHCO | — | S | N | CH |
| 33 | 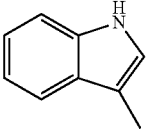 | 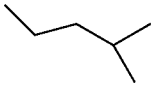 | 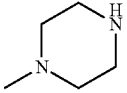 | NHCO | — | NH | N | N |
| 34 | 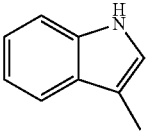 | 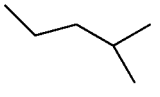 | 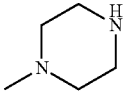 | NHCONH | — | S | N | CH |
| 35 | 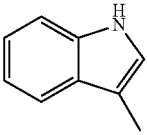 | 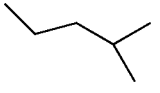 | 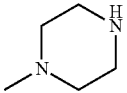 | NHCONH | — | NH | N | N |
| 36 | 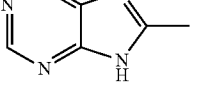 | 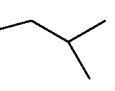 | 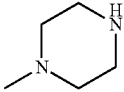 | NHCONH | — | S | CH | N |
| 37 | 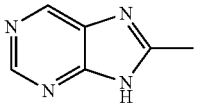 | 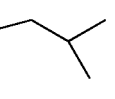 | 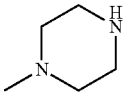 | NHCO | — | S | CH | N |
| 38 | 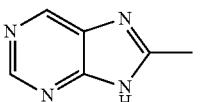 | 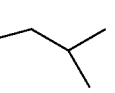 | 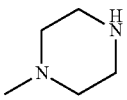 | NHCOO | — | S | CH | N |
| 39 | 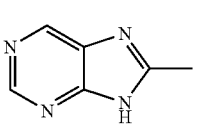 | 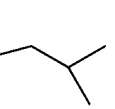 | 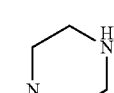 | NHCO | — | S | N | CH |
| 40 | 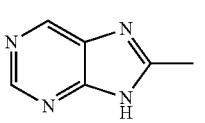 | 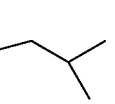 | 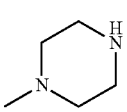 | NHCO | — | NH | N | N |
| 41 | 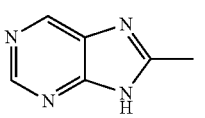 | 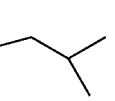 | 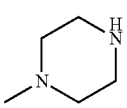 | NHCONH | — | S | N | CH |
| 42 | 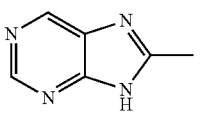 | 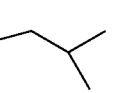 | 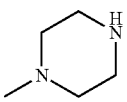 | NHCONH | — | NH | N | N |

TABLE A-continued

| No. | R1 | R2 | R3 | L | W | X | Y | Z |
|---|---|---|---|---|---|---|---|---|
| 43 | 3-indolyl | isopentyl | 4-methylpiperazin-1-yl | NHCONH | — | S | CH | N |
| 44 | 3-indolyl | isopentyl | 4-methylpiperazin-1-yl | NHCO | — | S | CH | N |
| 45 | 3-indolyl | isopentyl | 4-methylpiperazin-1-yl | NHCOO | — | S | CH | N |
| 46 | 3-indolyl | isopentyl | 4-methylpiperazin-1-yl | NHCO | — | S | N | CH |
| 47 | 3-indolyl | isopentyl | 4-methylpiperazin-1-yl | NHCO | — | NH | N | N |
| 48 | 3-indolyl | isopentyl | 4-methylpiperazin-1-yl | NHCONH | — | S | N | CH |
| 49 | 3-indolyl | isopentyl | 4-methylpiperazin-1-yl | NHCONH | — | NH | N | N |
| 50 | 8-methyl-9H-purin-yl | isopentyl | 4-methylpiperazin-1-yl | NHCONH | — | S | CH | N |
| 51 | 8-methyl-9H-purin-yl | isopentyl | 4-methylpiperazin-1-yl | NHCO | — | S | CH | N |
| 52 | 8-methyl-9H-purin-yl | isopentyl | 4-methylpiperazin-1-yl | NHCOO | — | S | CH | N |
| 53 | 8-methyl-9H-purin-yl | isopentyl | 4-methylpiperazin-1-yl | NHCO | — | S | N | CH |

TABLE A-continued
| No. | R1 | R2 | R3 | L | W | X | Y | Z |
|---|---|---|---|---|---|---|---|---|
| 54 | 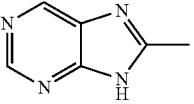 | 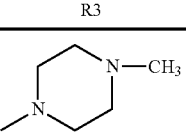 | 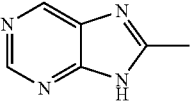 | NHCO | — | NH | N | N |
| 55 | 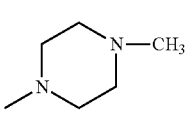 | 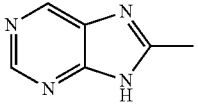 | 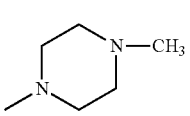 | NHCONH | — | S | N | CH |
| 56 | 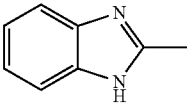 | 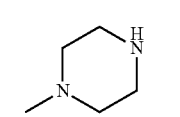 | 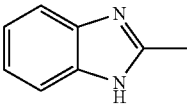 | NHCONH | — | NH | N | N |
| 57 | 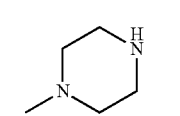 | 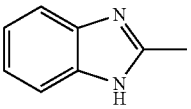 | 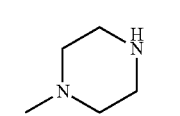 | NHCONH | — | S | CH | N |
| 58 | 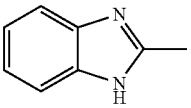 | 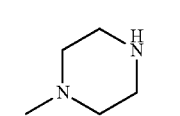 | 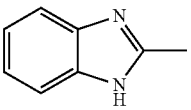 | NHCO | — | S | CH | N |
| 59 | 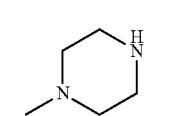 | 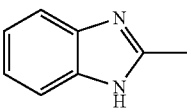 | 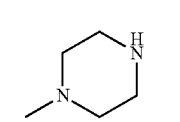 | NHCOO | — | S | CH | N |
| 60 | 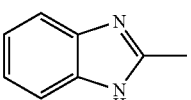 | 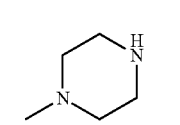 | 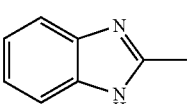 | NHCO | — | S | N | CH |
| 61 | 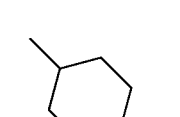 | 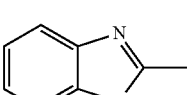 | 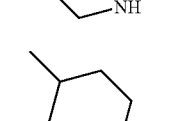 | NHCO | — | NH | N | N |
| 62 | 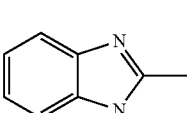 | 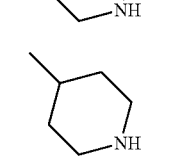 | | NHCONH | — | S | N | CH |
| 63 | | | | NHCONH | — | NH | N | N |
| 64 | | | | NHCONH | — | S | CH | N |
| 65 | | | | NHCO | — | S | CH | N |
| 66 | | | | NHCOO | — | S | CH | N |

TABLE A-continued

| No. | R1 | R2 | R3 | L | W | X | Y | Z |
|---|---|---|---|---|---|---|---|---|
| 67 | benzimidazol-2-yl | pentyl | 4-piperidinyl | NHCO | — | S | N | CH |
| 68 | benzimidazol-2-yl | pentyl | 4-piperidinyl | NHCO | — | NH | N | N |
| 69 | benzimidazol-2-yl | pentyl | 4-piperidinyl | NHCONH | — | S | N | CH |
| 70 | benzimidazol-2-yl | pentyl | 4-piperidinyl | NHCONH | — | NH | N | N |
| 71 | benzimidazol-2-yl | pentyl | 4-methylpiperazin-1-yl | NHCONH | — | S | CH | N |
| 72 | benzimidazol-2-yl | pentyl | 4-methylpiperazin-1-yl | NHCO | — | S | CH | N |
| 73 | benzimidazol-2-yl | pentyl | 4-methylpiperazin-1-yl | NHCOO | — | S | CH | N |
| 74 | benzimidazol-2-yl | pentyl | 4-methylpiperazin-1-yl | NHCO | — | S | N | CH |
| 75 | benzimidazol-2-yl | pentyl | 4-methylpiperazin-1-yl | NHCO | — | NH | N | N |
| 76 | benzimidazol-2-yl | pentyl | 4-methylpiperazin-1-yl | NHCONH | — | S | N | CH |
| 77 | benzimidazol-2-yl | pentyl | 4-methylpiperazin-1-yl | NHCONH | — | NH | N | N |
| 78 | benzimidazol-2-yl | pentyl | 4-piperidinyl | NHCONH | — | S | CH | N |

TABLE A-continued
| No. | R1 | R2 | R3 | L | W | X | Y | Z |
|---|---|---|---|---|---|---|---|---|
| 79 | 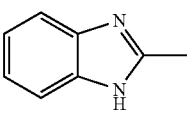 |  | 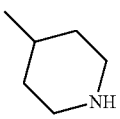 | NHCO | — | S | CH | N |
| 80 | 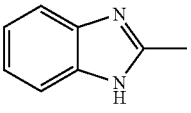 |  | 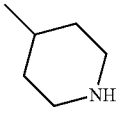 | NHCOO | — | S | CH | N |
| 81 | 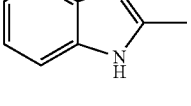 |  | 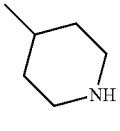 | NHCO | — | S | N | CH |
| 82 | 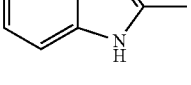 |  |  | NHCO | — | NH | N | N |
| 83 | 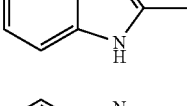 |  | 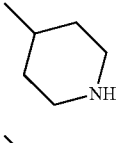 | NHCONH | — | S | N | CH |
| 84 | 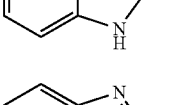 |  | 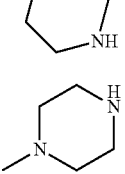 | NHCONH | — | NH | N | N |
| 85 | 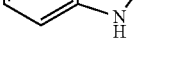 |  |  | NHCONH | — | S | CH | N |
| 86 | 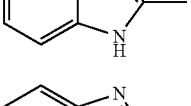 |  |  | NHCO | — | S | CH | N |
| 87 | 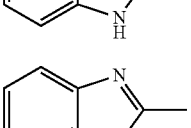 |  |  | NHCOO | — | S | CH | N |
| 88 | 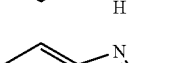 |  |  | NHCO | — | S | N | CH |
| 89 | 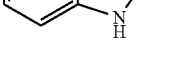 |  |  | NHCO | — | NH | N | N |
| 90 | 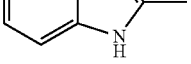 |  |  | NHCONH | — | S | N | CH |
| 91 | 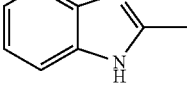 |  |  | NHCONH | — | NH | N | N |

TABLE A-continued
| No. | R1 | R2 | R3 | L | W | X | Y | Z |
|---|---|---|---|---|---|---|---|---|
| 92 | 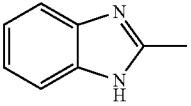 | 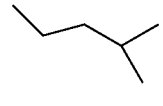 | 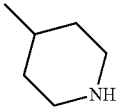 | NHCONH | — | S | CH | N |
| 93 | 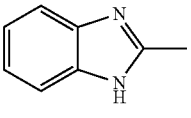 | 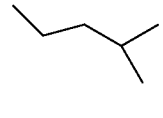 | 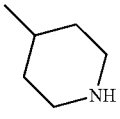 | NHCO | — | S | CH | N |
| 94 | 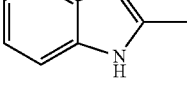 | 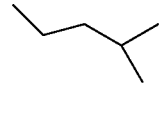 | 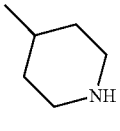 | NHCOO | — | S | CH | N |
| 95 | 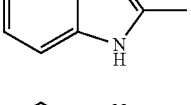 |  | 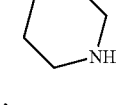 | NHCO | — | S | N | CH |
| 96 | 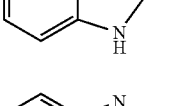 |  | 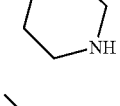 | NHCO | — | NH | N | N |
| 97 | 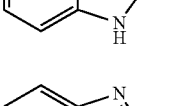 |  | 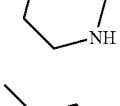 | NHCONH | — | S | N | CH |
| 98 | 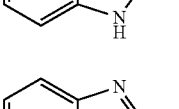 | 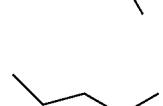 | 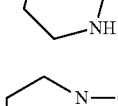 | NHCONH | — | NH | N | N |
| 99 | 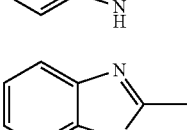 | 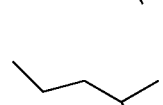 | 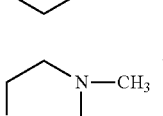 | NHCONH | — | S | CH | N |
| 100 | 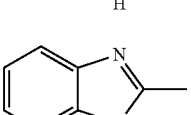 | 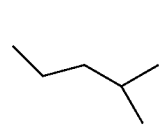 | 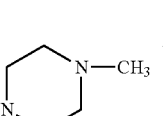 | NHCO | — | S | CH | N |
| 101 | 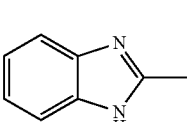 | 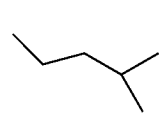 | 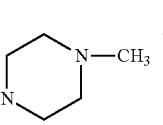 | NHCOO | — | S | CH | N |
| 102 | 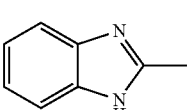 | 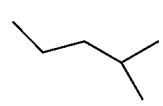 | 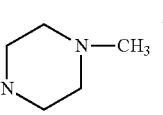 | NHCO | — | S | N | CH |
| 103 |  |  |  | NHCO | — | NH | N | N |

TABLE A-continued

| No. | R1 | R2 | R3 | L | W | X | Y | Z |
|---|---|---|---|---|---|---|---|---|
| 104 | 2-methylbenzimidazole | isopentyl | 4-methyl-1-methylpiperazine | NHCONH | — | S | N | CH |
| 105 | 2-methylbenzimidazole | isopentyl | 4-methyl-1-methylpiperazine | NHCONH | — | NH | N | N |
| 106 | 2-methylbenzimidazole | isopentyl | 4-methylpiperidine | NHCONH | — | S | CH | N |
| 107 | 2-methylbenzimidazole | isopentyl | 4-methylpiperidine | NHCO | — | S | CH | N |
| 108 | 2-methylbenzimidazole | isopentyl | 4-methylpiperidine | NHCOO | — | S | CH | N |
| 109 | 2-methylbenzimidazole | isopentyl | 4-methylpiperidine | NHCO | — | S | N | CH |
| 110 | 2-methylbenzimidazole | isopentyl | 4-methylpiperidine | NHCO | — | NH | N | N |
| 111 | 2-methylbenzimidazole | isopentyl | 4-methylpiperidine | NHCONH | — | S | N | CH |
| 112 | 2-methylbenzimidazole | isopentyl | 4-methylpiperidine | NHCONH | — | NH | N | N |

— is a single bond

The compound according to the present invention is preferably selected from the group consisting of
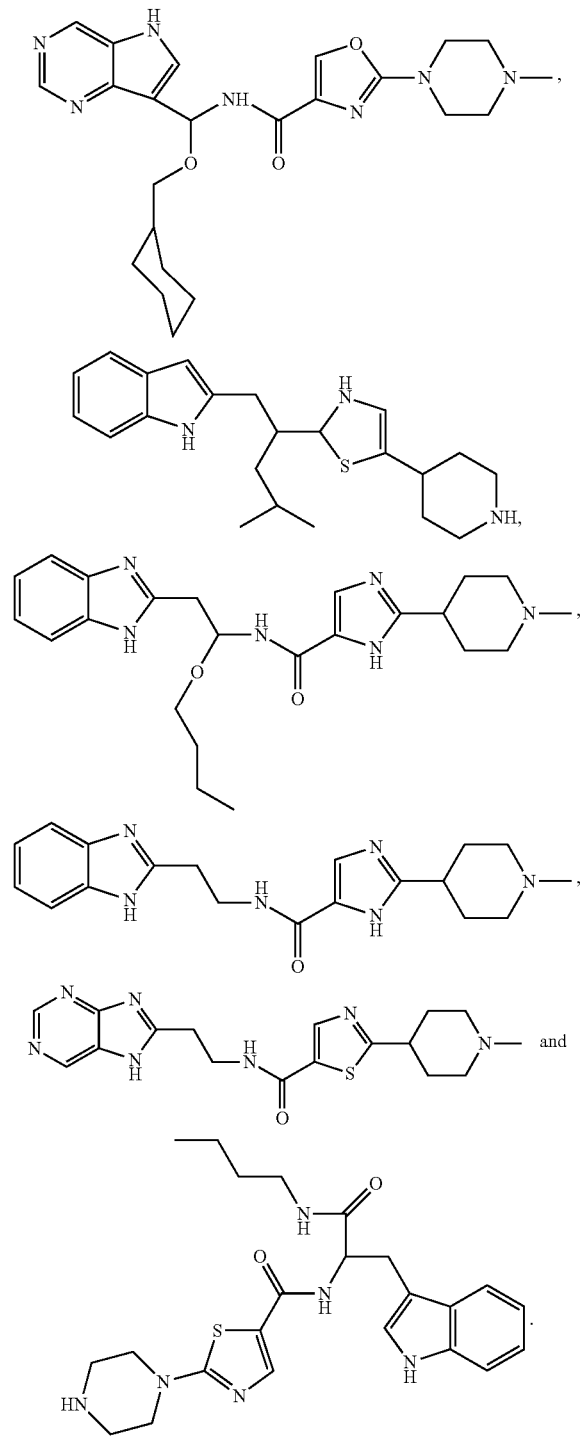
Compounds which can be summarized under formula (Ia) may have further the following substituents and structures:
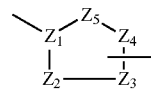
may be selected from the group consisting of
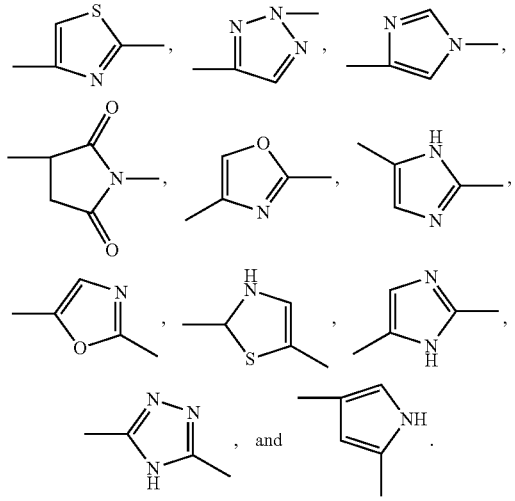
Formula (Ia) may additionally comprise the following structures:
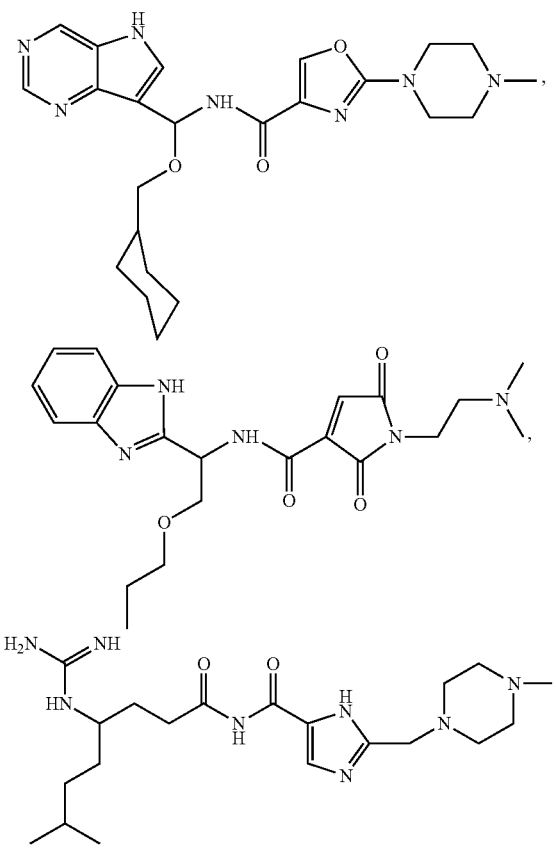

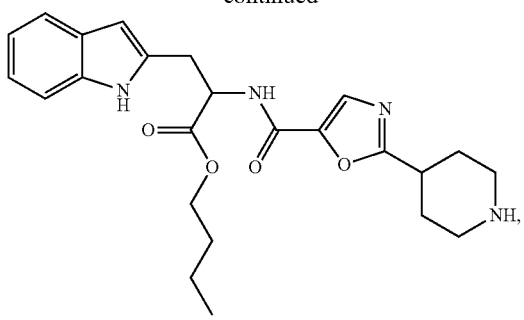

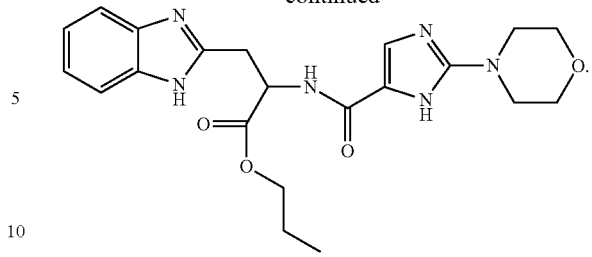

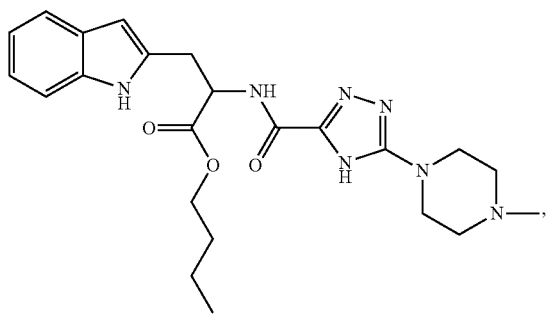

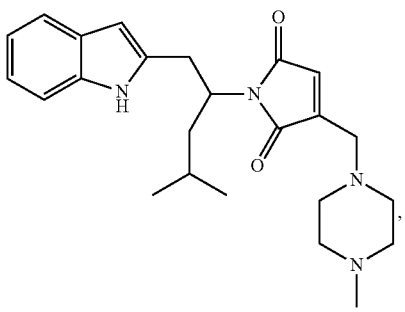

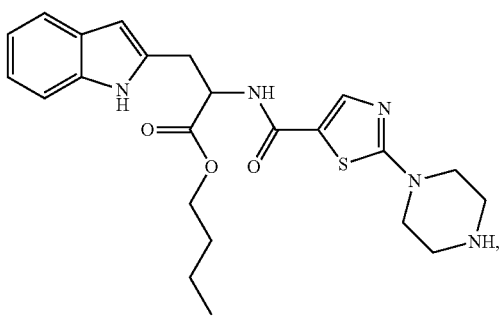

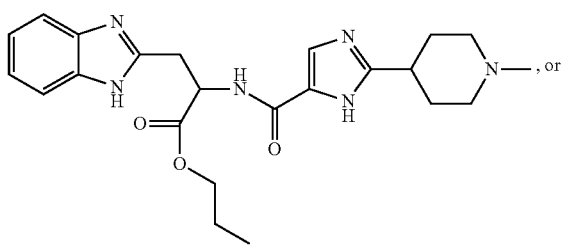

The compounds of the present invention can be used for treating, ameliorating and/or preventing synucleopathies.

The synucleopathies are preferably selected from the group consisting of Parkinson's Disease, Parkinson's Disease with Dementia, Dementia with Lewy bodies, Pick's Disease, Down's Syndrome, Multiple System Atrophy, Amylotrophic Lateral Sclerosis (ALS) and Hallervorden-Spatz Syndrome.

Another aspect of the present invention relates to a pharmaceutical preparation comprising an effective amount of a compound according to the present invention or a pharmaceutically acceptable salt thereof or a pharmaceutically acceptable solvate of said compound or salt, and one or more pharmaceutically acceptable excipients.

The compounds of the present invention or a pharmaceutically acceptable salt thereof may be formulated by following any number of techniques known in the art of drug delivery. The compounds or pharmaceutically acceptable salts thereof may of course be administered by a number of means keeping in mind that all formulations are not suitable for every route of administration. They can be administered in solid or liquid form. The application may be oral, rectal, nasal, topical (including buccal and sublingual) or by inhalation. The compounds of the invention or a pharmaceutically acceptable salt thereof may be administered together with conventional pharmaceutically acceptable adjuvants, carriers and/or diluents. The solid dosage forms comprise tablets, capsules, powders, pills, pastilles, suppositories, gels and granular forms of administration. They may also include carriers or additives, such as flavors, dyes, diluents, softeners, binders, preservatives, lasting agents and/or enclosing materials. Liquid forms of administration include solutions, suspensions and emulsions. These may also be offered together with the above-mentioned additives.

Solutions and suspensions of the compounds of the invention or pharmaceutically acceptable salts thereof (provided of course that these solutions and suspensions have a suitable viscosity) may be injected. If the suspension is too viscous for injection the pharmaceutical preparation may be implanted using devices designed for such purposes. Sustained release forms are generally administered via parenteral or enteric means. Parenteral administration is another route of administration of the compounds of the present invention or pharmaceutically acceptable salts thereof.

The administration of the compounds of the present invention may involve an oral dosage form. Oral dose formulations are preferably administered once or twice daily, three times daily in the form of a capsule or tablet, for instance, or alternatively as an aqueous based solution. If the compounds of the present invention are administered intravenously, the administration may occur either daily, continuously, once a week or three times a week.

It is also possible to provide pharmaceutical compositions which in addition to the compounds of the present invention comprise other substances which are suited for treating, preventing or relieving the symptoms of synucleopathies and Parkinson's-like disorders. These combinations may be administered in solid or liquid form in a single formulation or composition or in separate formulations or compositions.

According to a preferred embodiment of the present invention the pharmaceutical compositions contain from about 0.01 mg to about 5.0 g, preferably from about 0.05 mg to 2 g, more preferably from about 0.5 mg to 1 g, even more preferably from about 1 mg to 500 mg, of the compound of the present invention. The compounds of the present invention can be administered to a patient in an amount of about 0.01 mg to about 5 g, preferably of about 0.05 mg to 2 g, more preferably from about 0.5 mg to 1 g, even more preferably from about 1 mg to about 500 mg per kg body ledge weight.

The compounds of the present invention may also be provided as sustained release oral formulations. These formulations generally comprise the compounds of the invention having decreased solubility in order to delay absorption into the bloodstream. In addition, these formulations may include other components, agents, carriers, etc., which may also serve to delay absorption of the compounds. Microencapsulation, polymeric entrapment systems, and osmotic pumps, which may or may not be bioerodible, may also be used to allow delayed or controlled diffusion of the compounds from a capsule or matrix.

As used herein, the term "effective amount" in the context of treating or preventing alpha-synucleopathies or Parkinson's-like disorders, especially PD, relates to the administration or addition of an amount of the compound of the present invention that is effective for the prevention and/or treatment of existing synucleopathies or Parkinson's-like disorder. The effective amount will vary depending on the health and physical condition of the individual to be treated, the taxonomic group of the individual to be treated, the formulation of the composition, the assessment of the medical situations and other relevant factors.

Another aspect of the present invention relates to the use of a compound according to the present invention or a pharmaceutically acceptable salt thereof or a pharmaceutically acceptable solvate of said compound or salt for the manufacture of a medicament for treating, ameliorating and/or preventing synucleopathies.

The synucleopathies are preferably selected from the group consisting of Parkinson's Disease, Parkinson's Disease with Dementia, Dementia with Lewy bodies, Pick's Disease, Down's Syndrome, Multiple System Atrophy, Amylotrophic Lateral Sclerosis (ALS) and Hallervorden-Spatz Syndrome.

A further aspect of the present invention relates to a method for producing the compounds of the present invention.

The compounds of formula (I) as well as of formula (Ia) may be prepared by the methods of known chemical reactions and procedures, some from starting materials which are well known in the art. General preparative methods described in "Introduction to organic chemistry" by Streitwieser et al. (Macmilan Publishers 4$^{th}$ Edition, 1992) can be followed to aid one skilled in the art in synthesizing these compounds, with more detailed examples being provided in the reaction schemes below and in the examples.

Substituted and unsubstitued oxadiazoles, thiazoles, triazoles, imidazoles, thiatriazoles, thiophenes, pyrroles, pyrrolines, pyrazoles may be prepared by using standard methods (see, for example, A R Katritzky, Comprehensive Heterocyclic Chemistry II, Vol. 5. M H Palmer. Heterocyclic Compounds, Arnold Ltd, London (1967)).

Overall reaction schemes for the synthesis of specific compounds of formula I are shown below.

The synthesis of oxazoles as exemplified in the example leading to compound A can be accomplished in the condensation reaction of two fragments, one containing the indole ring (compound 7) and one containing the ozazole scaffold (compound 13), followed by deblocking of the piperedine moiety as shown in compound 11.

Compound 7 is a general intermediate from which other analogs can be prepared. For example the triazole compound B can be synthesized via the compound 7 intermediate via amidation of compound 18 following deblocking reactions as shown for compound A.

Alternatively an analog containing the thiazole scaffold can be made via the compound 7 intermediate and intermediate compound 23 having the thiazole ring.

A reaction route leading an imide ring scaffold and having an isobutene side chain in place of the butyl ester group can be prepared as shown in the reaction scheme involving intermediate compounds 25-34.

Still other variations are shown in the scheme involving the synthesis of compounds E and F.

Reaction schemes for the synthesis of inhibitors:

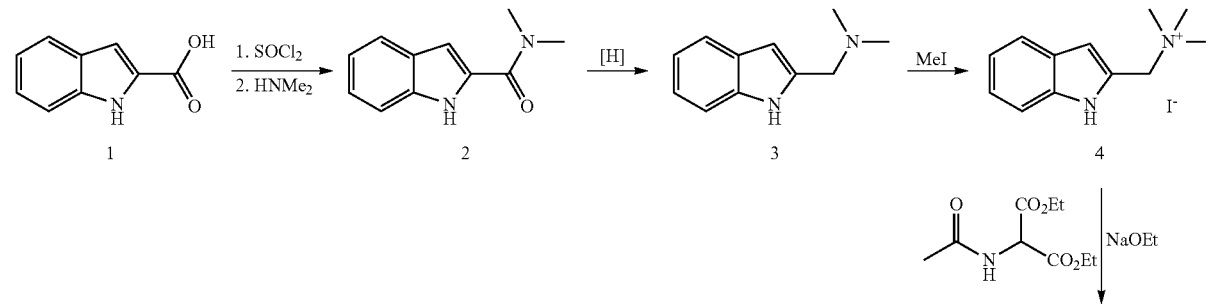

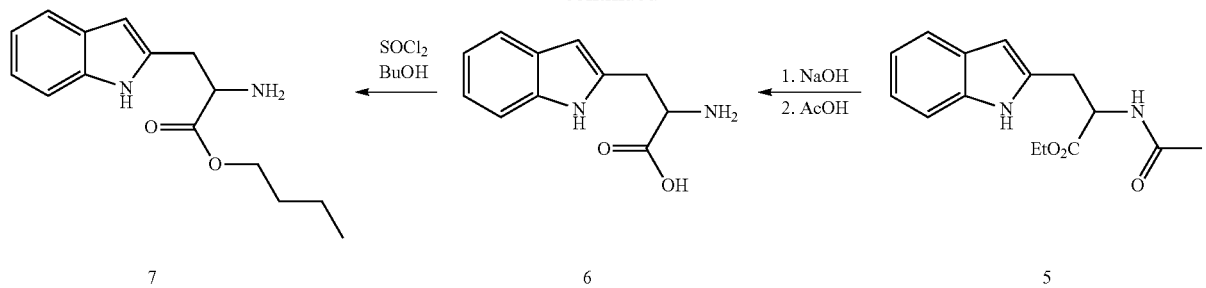
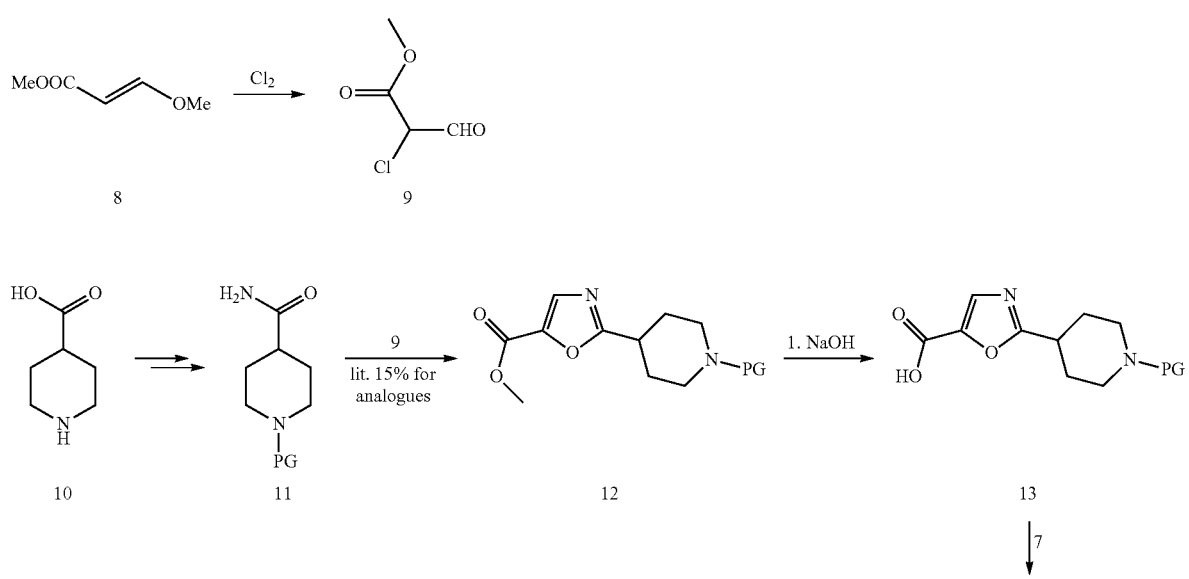
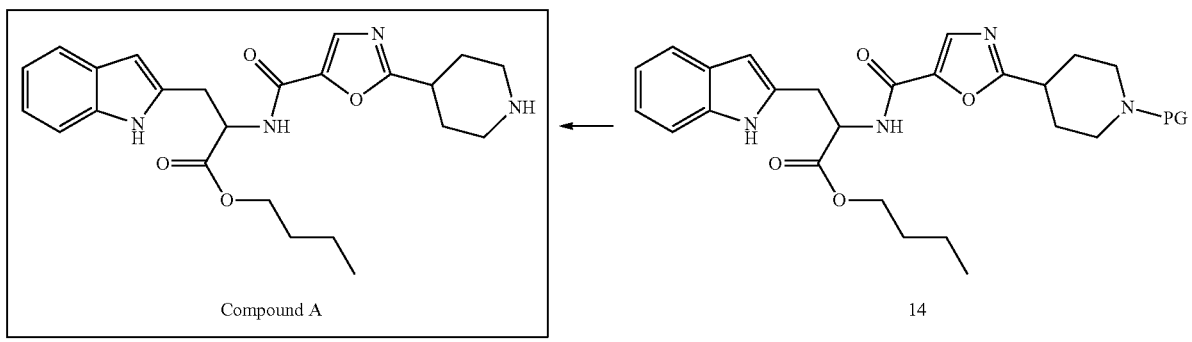
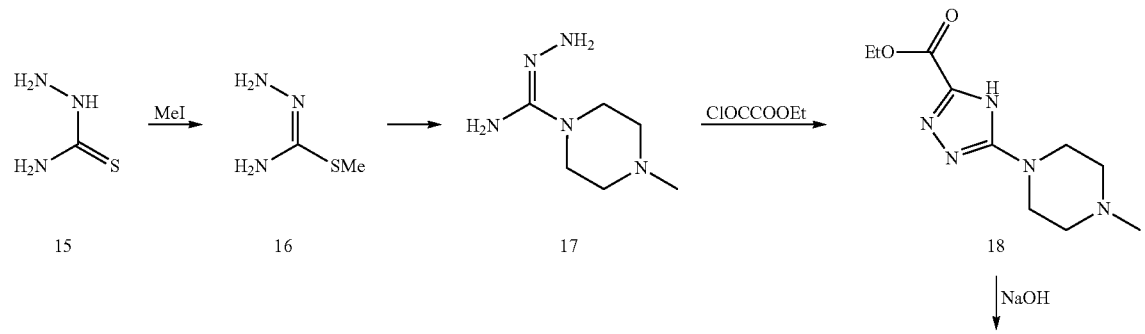

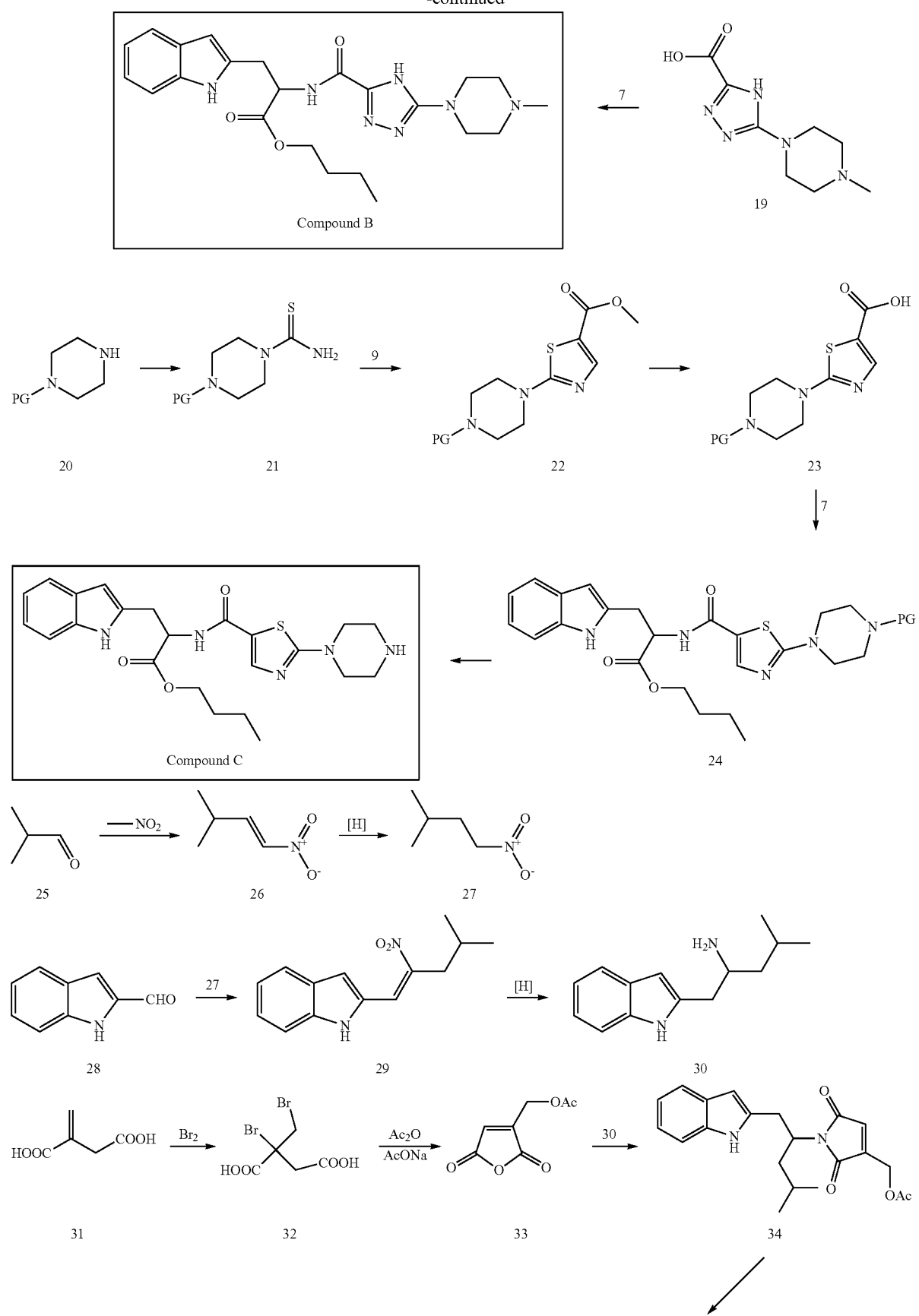

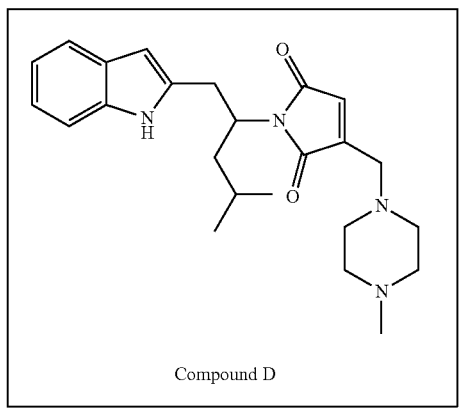

Compound D

A modification of the above scheme starting with tryptophan is shown below. This modification significantly reduces the number of steps needed to obtain the final products.

The reaction of equimolar quantities of tryptophan (compound 1) with butanol yield compound 2. The amino group in piperazine carboxylic acid can be blocked by standard methods described in T W Greene et. al. (Protective groups in organic synthesis, Third edition, Wiley Interscience (1999)), which can be further reacted with compound 9 in the general scheme to obtain the oxazole intermediate. Deesterification of 12 with sodium hydroxide yields the carboxylic acid 13. Reaction of intermediate 13 with compound 2 yields the intermediate 14 and deblocking of 14 gives the final product (compound A1).

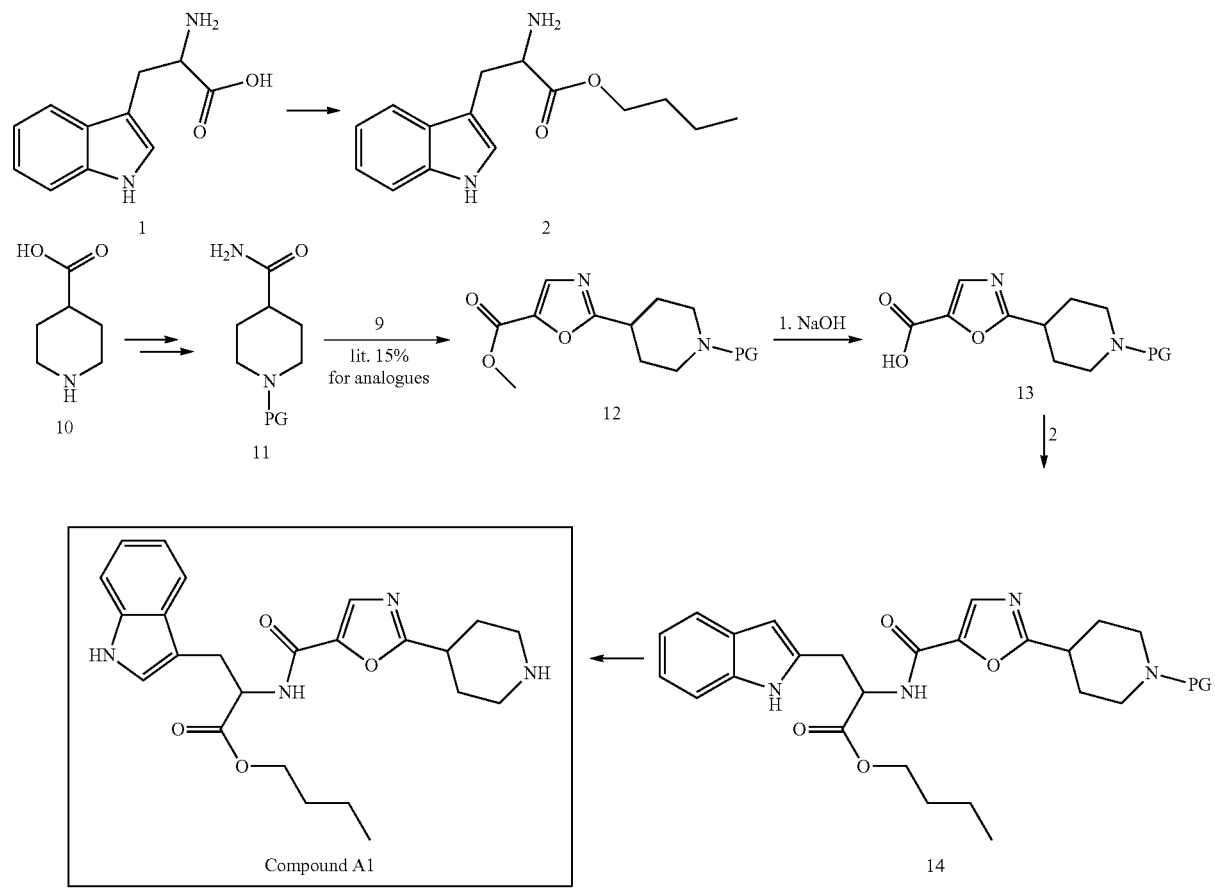

A variation of the above synthetic procedure as shown below yields the triazole intermediate compound 18 which can be further reacted similar to compound A1 using the intermediate compound 2 to give the final triazole analog compound B1.
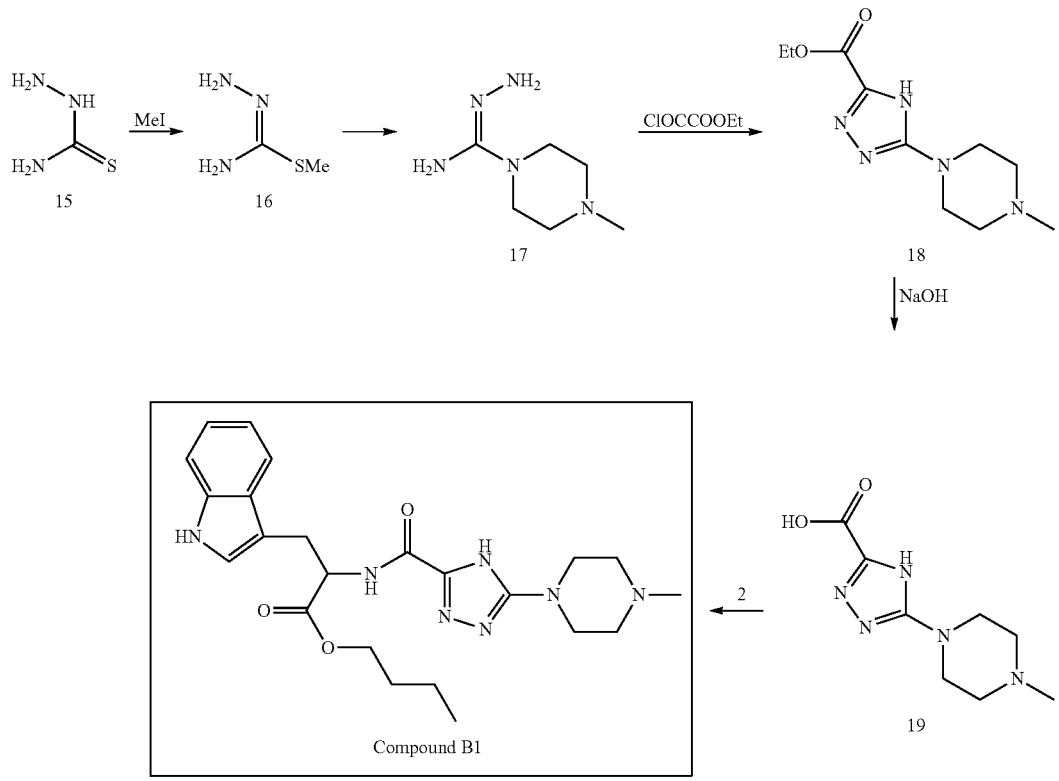
Alternatively the procedures can be adapted to obtain a thiazole analog as shown in the example of the reaction scheme below.
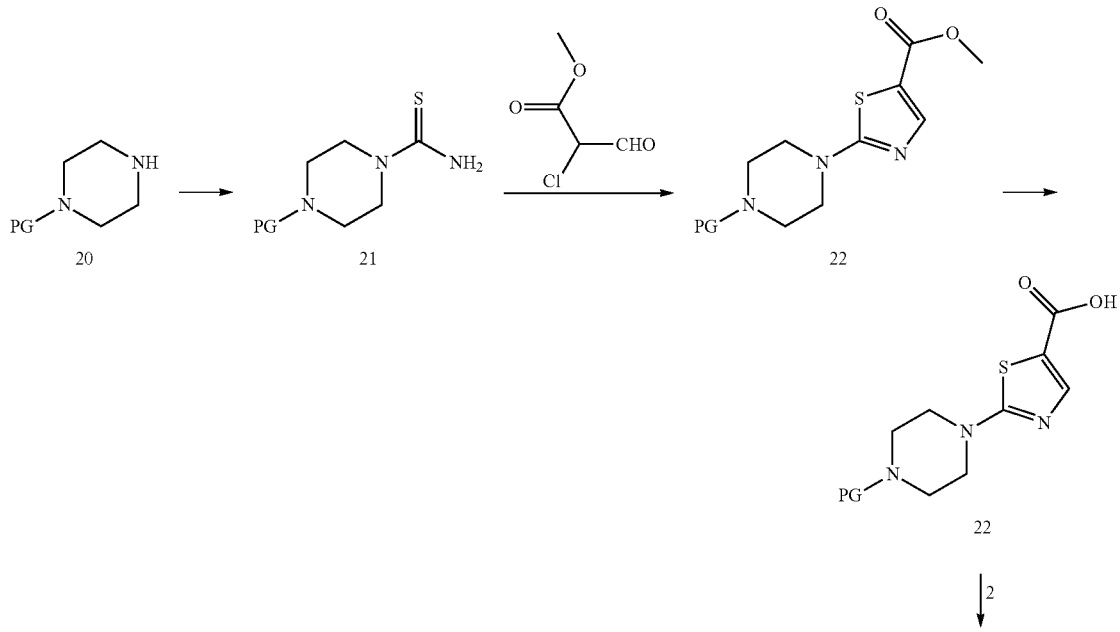

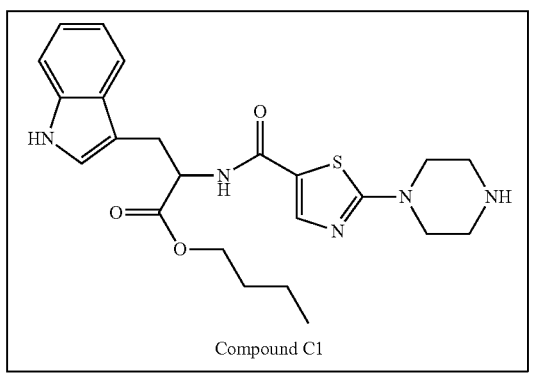

Compound C1

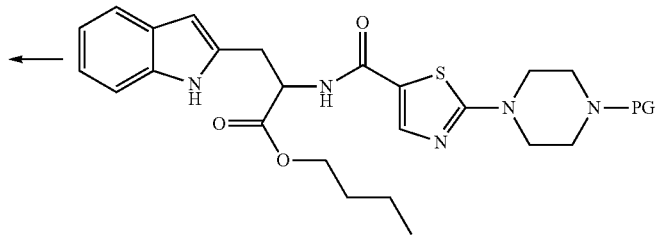

24

All reactions can be performed in flam-dried or oven dried glassware under positive pressure of argon or nitrogen. The reaction vessels were stirred magnetically. Sensitive liquids and solutions were transferred via syringe and introduced into the reaction vessels through rubber septa.

Another aspect of the present invention relates to a method for treating, ameliorating and/or preventing synucleopathies and/or their symptoms by administering to an individual suffering or being at risk to suffer from said synucleopathies an effective amount of a compound or a pharmaceutical preparation according to the present invention.

A further aspect of the present invention relates to the use of the compounds of the present invention as biomarkers. The compounds of the present invention can be used, when labelled accordingly (e.g. radioactively), in positron emission tomography (PET) for determining whether a patient comprises α-synuclein or any other plaques to which the compounds of the present invention are able to bind. This allows the localization of the plaques within the body and allows also to identify the amount of said plaques. This allows the medical doctor to treat or prevent conditions associated with synucleopathy. Methods to label compounds are accordingly well known in the art.

The present invention is further illustrated by the following figures and examples without being restricted thereto.

FIG. 1 shows patterns of alpha-synuclein accumulation in the brains of patients with DLB and PD. (A) Immunoblot analysis showing increased alpha-syn oligomers accumulation in the membrane fractions of LBD cases compared to controls and AD. (B-E) By immunocytochemistry, alpha-syn accumulates in synapses, neuronal cell bodies and axons. (F) Molecular dynamics studies illustrating alpha-syn docking to the membranes.

EXAMPLES

Example 1

The chemical synthesis of the compounds having formula (I) as defined above is exemplified by the synthesis of the compound having the following structure:

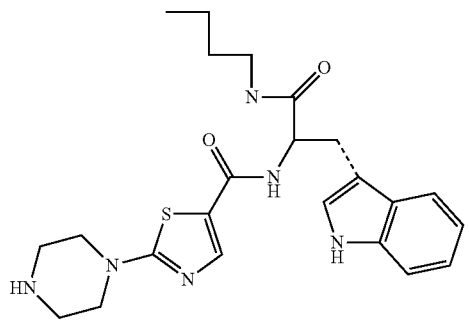

Figure 8:
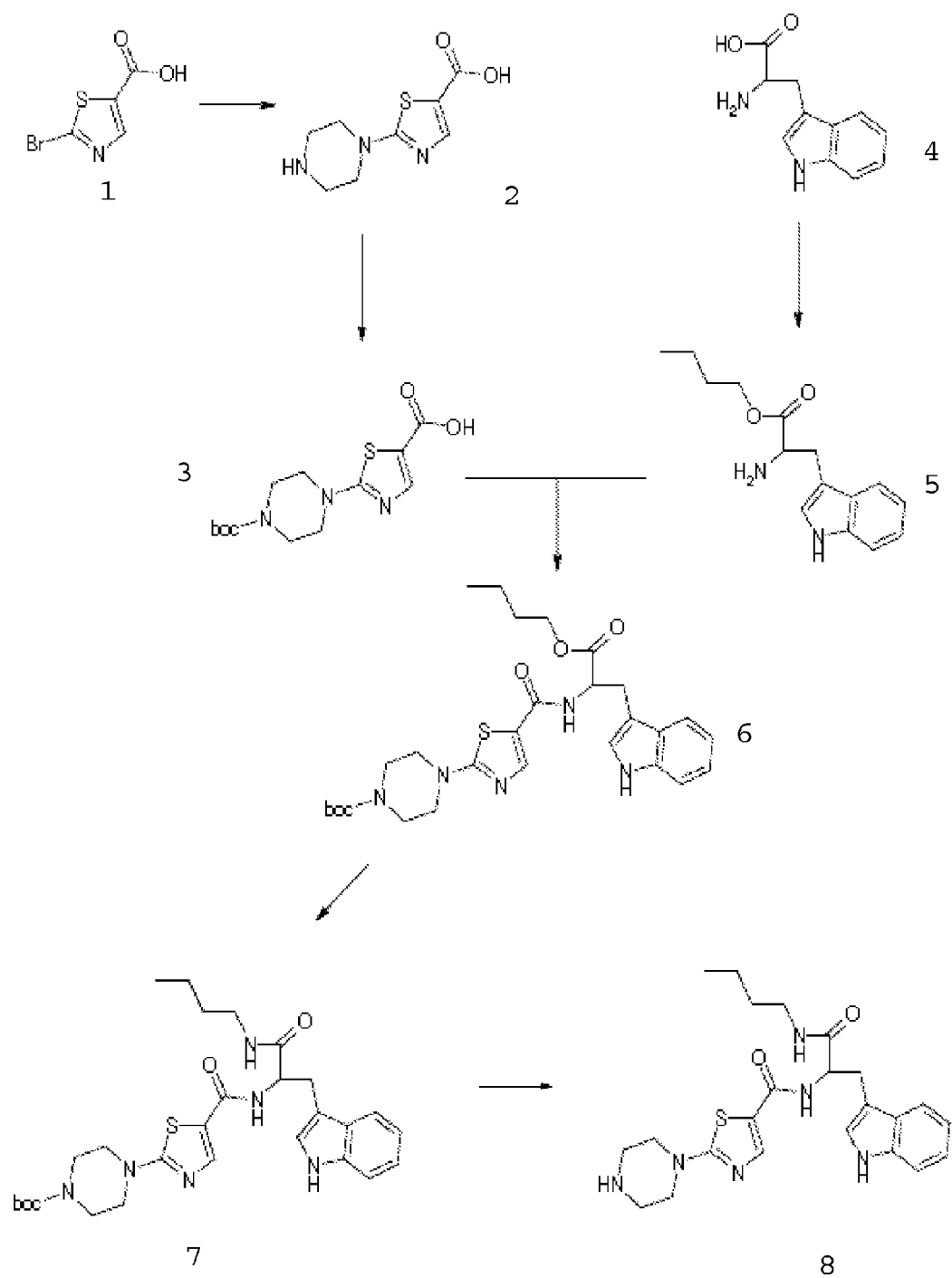
FIG. 8 shows an overview of the chemical synthesis of a compound according to the present invention.

The synthesis scheme is depicted in FIG. 8.

1. Synthesis of 2-piperazinyl-thiazole-5-carboxylic acid 2

2-Bromothiazole carboxylic acid 1 (1 g; 4.8 mmol) and piperazine (6.2 g; 72 mmol; 24 equiv.) were dissolved in dioxane, K2CO3 (3.32 g; 24 mmol; 5 equiv.) was added and the suspension was refluxed over night. The solvent was removed at the rotary evaporator, the residue dissolved in ethanol, filtered and recrystallized. The crude product was dried at the oil pump and directly used in the following step.

2. Protection of 2 with Boc

Crude 1, triethylamine (24 mmol; 3.4 ml) and di-tert. butyl-dicarbonate (14.4 mmol; 3.14 g) were dissolved in methanol and refluxed over night. The solvents were removed at the rotary evaporator and the residue was chromatographed over a short silica gel column.

Yield of 3: 1.18 g (72% over two steps).

3. Synthesis of Tryptophane Butylester 5

L-Tryptophane (5 g; 24.5 mmol) and thionyl chloride (73.5 mmol; 5.3 ml) were dissolved in n-butanol (80 ml) and stirred at 100° C. over night. The product 5 precipitated after cooling to room temperature, was filtered off and washed with ice cold butanol and petrol ether. The product was dried at the oil pump, yielding 5.8 g of 5 (91%).

4. Coupling of 3 and 5 a.) Formation of the Succinimidyl Ester
2-(1-Boc-piperazin-4-yl)-thiazole-5-carboxylic acid 3 (250 mg; 0.8 mmol), Nhydroxysuccinimide (110 mg; 0.95 mmol), diisopropylcarbodiimide (0.15 ml; 0.95 mmol) and DMAP (5 mg; 0.04 mmol) were dissolved in dry dichloromethane and stirred at room temperature over night (reaction monitoring by thin layer chromatography). A 1 M aqueous solution, of KHSO4 was added, the precipitate was removed by filtration and the organic phase was extracted with water.

b.) Coupling with 5
The crude succinimidyl ester, tryptophane butyl ester 5 (250 mg; 0.96 mmol) and triethylamine (0.65 ml) were dissolved in dry THF (5 ml) and stirred at 50° C. for 24 h. THF was removed in vacuo. The residue was taken up in dichloromethane and extracted with aqueous 1 M KHSO4. Crude 6 was used in the following step without purification.

5. Formation of n-butyl amide 7

Crude 6 was dissolved in 10 ml n-butylamine and refluxed over night (reaction monitoring by HPLC-MS). The solvent n-butylamine was removed at the rotary evaporator, the residue was dried at the oil pump, recrystallized from methanol and purified by column chromatography (DCM→MeOH). Yield: 340 mg (0.61 mmol; 64% over two steps)

6. Deprotection of 7

Figure 9:
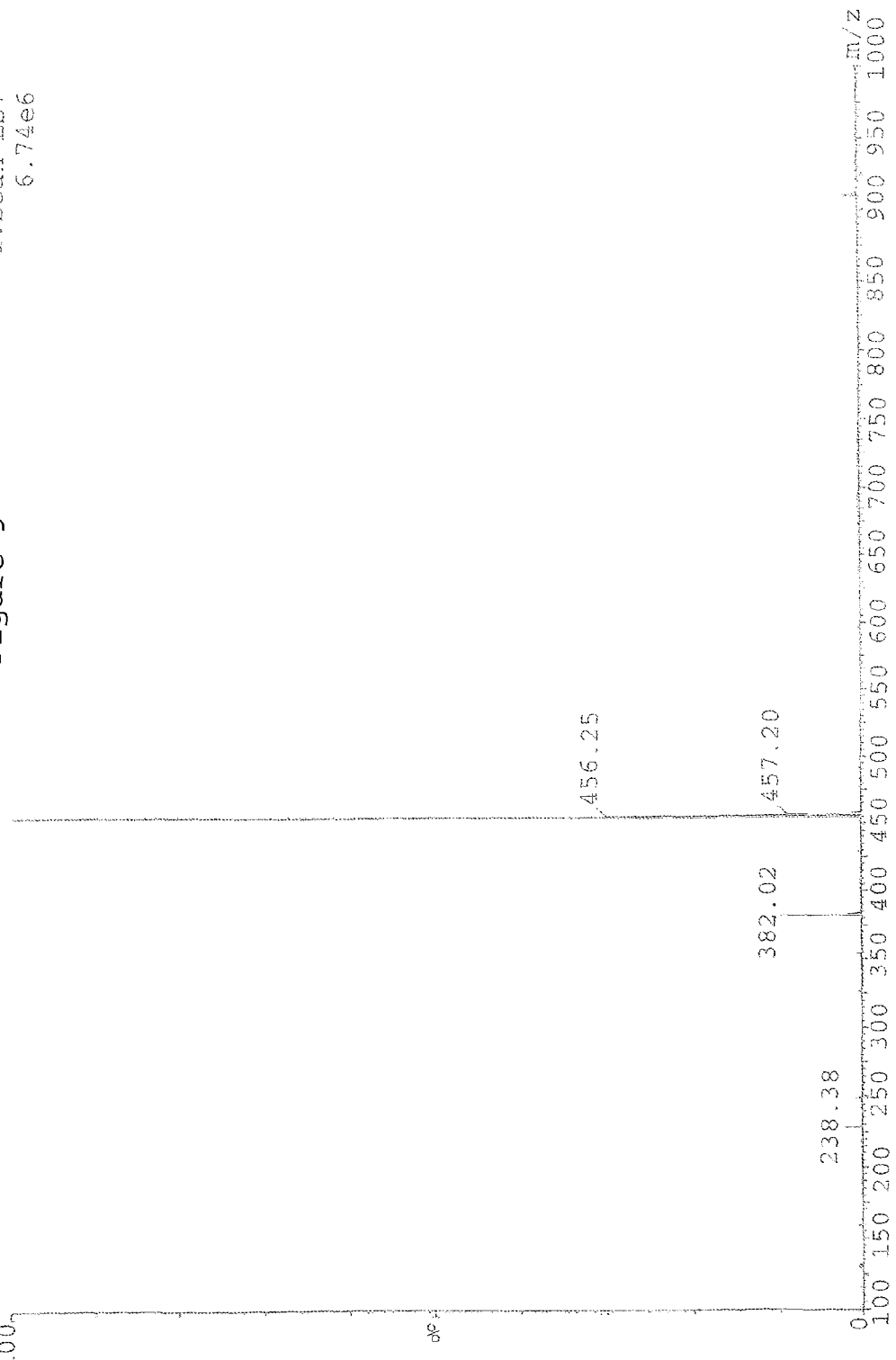
FIG. 9 shows a mass spectrum of the product obtained in example 1.

The Boc-protected 6 was dissolved in 45% THF, 45% trifluoroacetic acid and 10% water and the THF and TFA were slowly removed at the rotary evaporator. The residue was lyophilized, precipitated in diethyl ether and purified by chromatography on silica gel (DCM→MeOH). Yield: 223 mg (0.49 mmol; 80%). The product obtained was subjected to mass spectrometry (see FIG. 9).

Example 2

The compounds of formula Ia

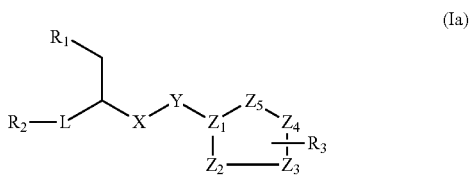

(Ia)

may be prepared by the methods of known chemical reactions and procedures, some from starting materials which are well known in the art.

Overall reaction schemes for the synthesis of specific compounds of formula I are shown below.

The synthesis of oxazoles as exemplified in the example leading to compound A can be accomplished in the condensation reaction of two fragments, one containing the indole ring (compound 7) and one containing the ozazole scaffold (compound 13), followed by deblocking of the piperedine moiety as shown in compound 11.

Compound 7 is a general intermediate from which other analogs can be prepared. For example the triazole compound B can be synthesized via the compound 7 intermediate via amidation of compound 18 following deblocking reactions as shown for compound A.

Alternatively an analog containing the thiazole scaffold can be made via the compound 7 intermediate and intermediate compound 23 having the thiazole ring.

A reaction route leading an imide ring scaffold and having an isobutene side chain in place of the butyl ester group can be prepared as shown in the reaction scheme involving intermediate compounds 25-34.

Still other variations are shown in the scheme involving the synthesis of compounds E and F.

Reaction schemes for the synthesis of inhibitors:

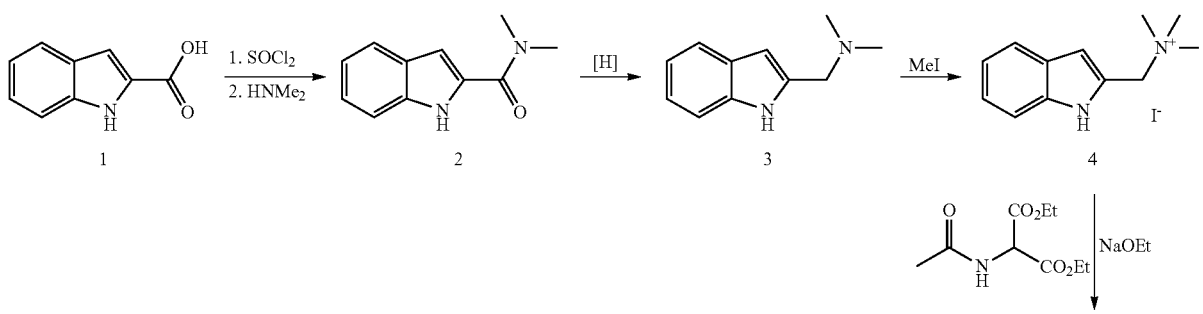

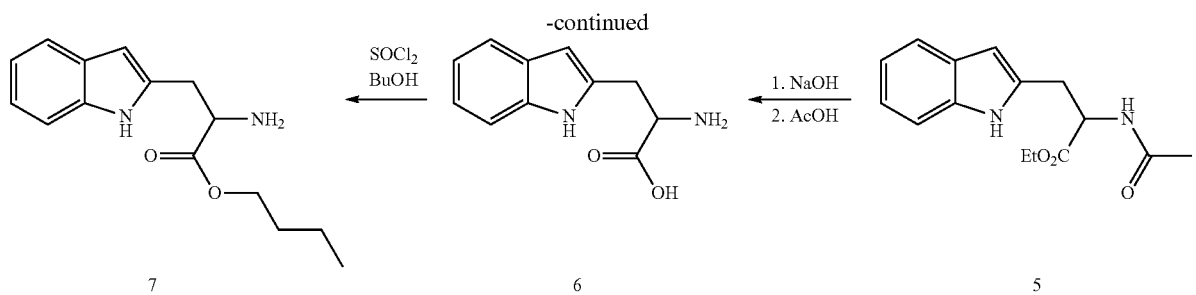
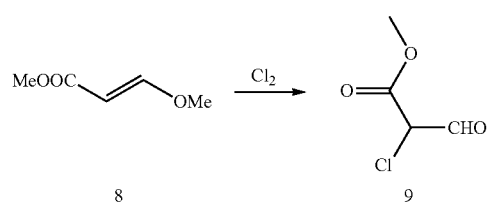
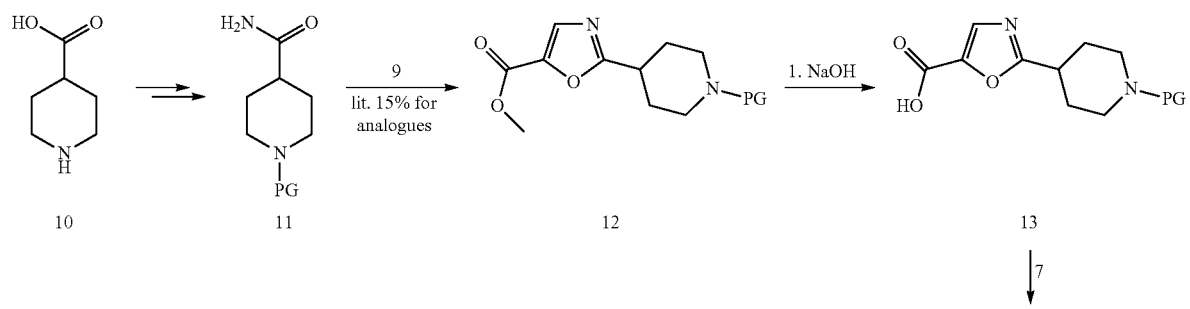
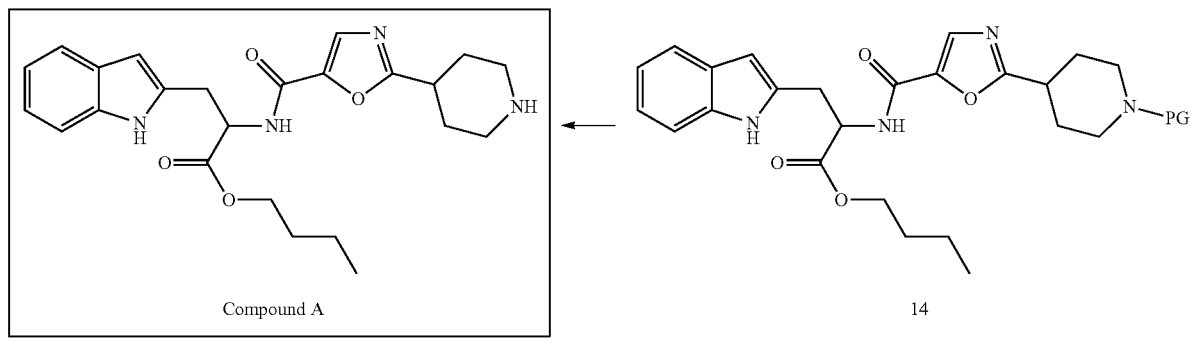
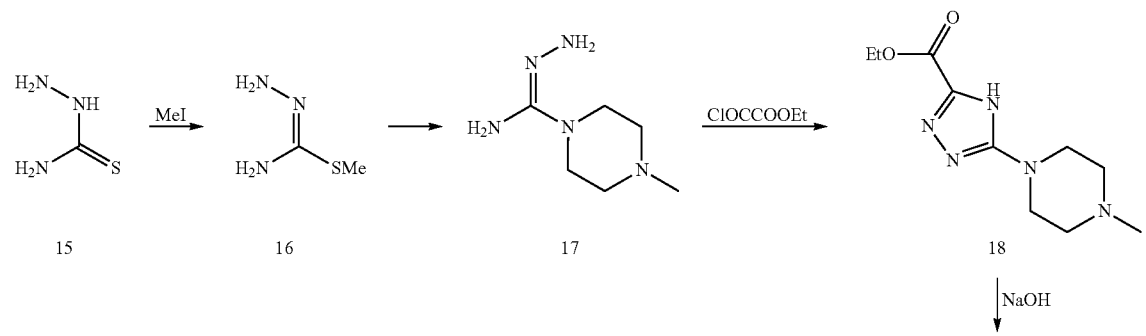

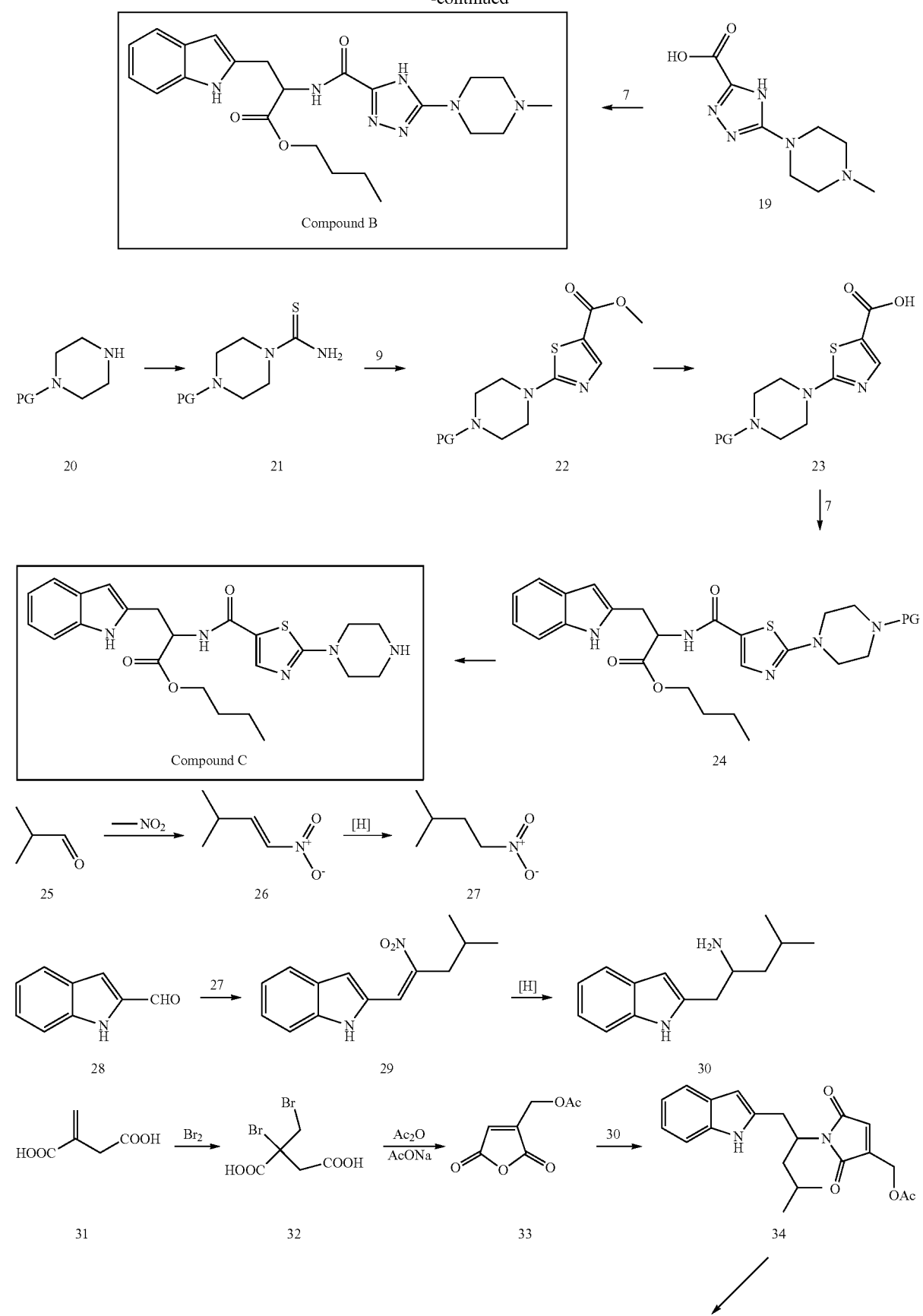

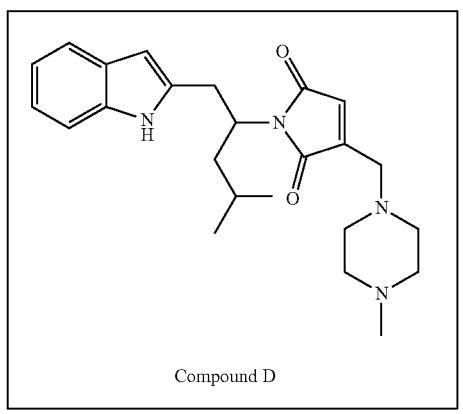
Compound D

A modification of the above scheme starting with tryptophan is shown below. This modification significantly reduces the number of steps needed to obtain the final products.

The reaction of equimolar quantities of tryptophan (compound 1) with butanol yields compound 2. The amino group in piperazine carboxylic acid can be blocked by standard methods described in T W Greene et. al. (Protective groups in organic synthesis, Third edition, Wiley Interscience (1999)), which can be further reacted with compound 9 in the general scheme to obtain the oxazole intermediate. Deesterification of 12 with sodium hydroxide yields the carboxylic acid 13. Reaction of intermediate 13 with compound 2 yields the intermediate 14 and deblocking of 14 gives the final product (compound A1).

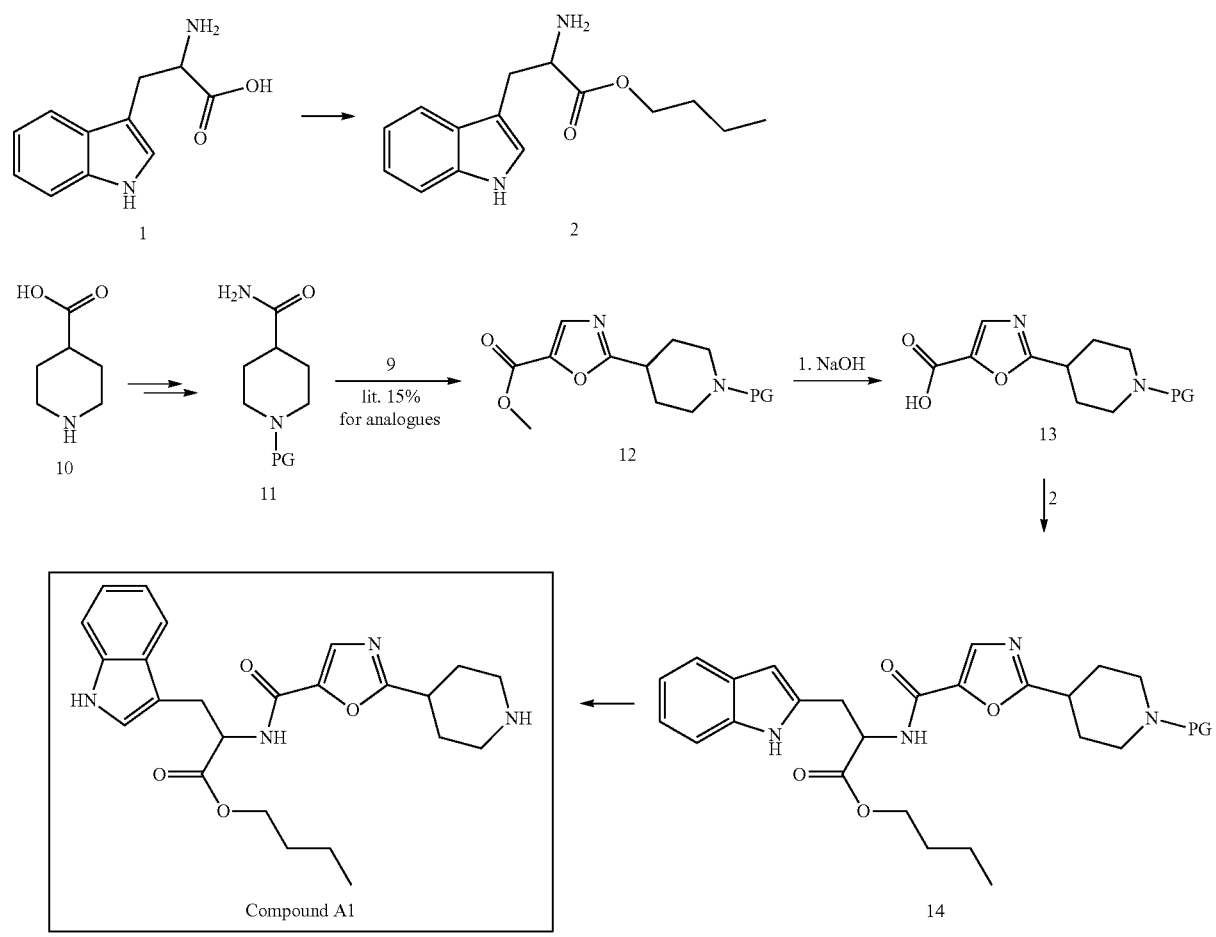

A variation of the above synthetic procedure as shown below yields the triazole intermediate compound 18 which can be further reacted similar to compound A1 using the intermediate compound 2 to give the final triazole analog compound B1.
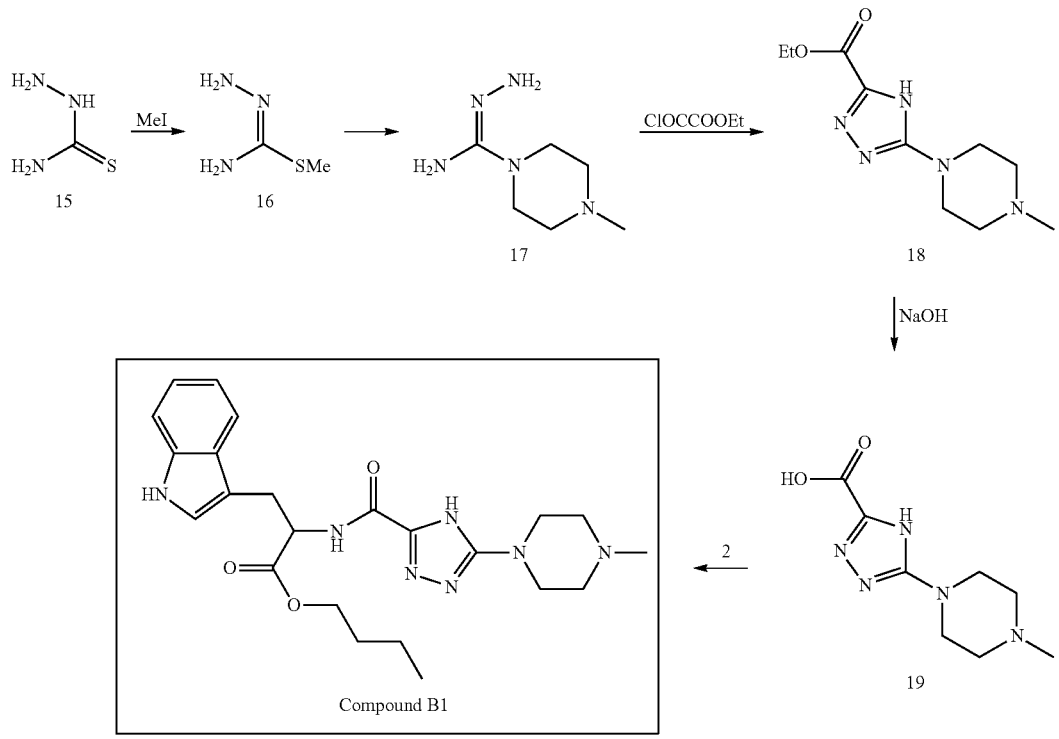
Alternatively the procedures can be adapted to obtain a thiazole analog as shown in the example of the reaction scheme below.
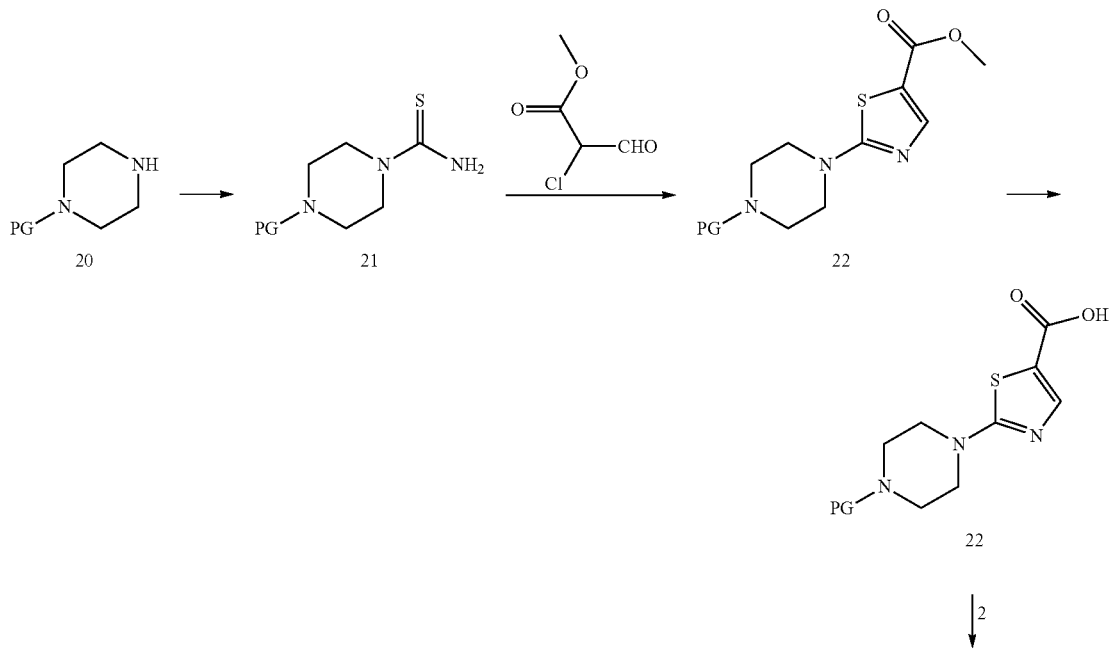

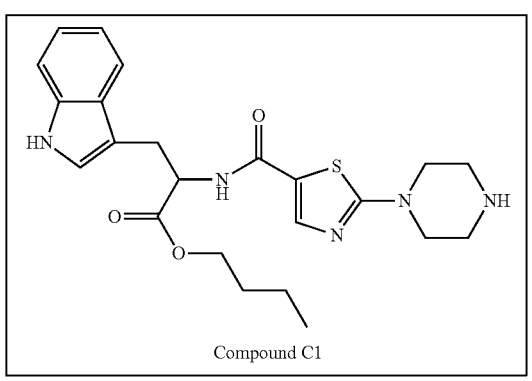

Compound C1

←

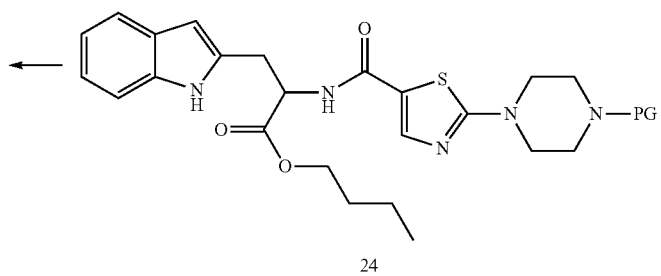

24

All reactions were performed in flam-dried or oven dried glassware under positive pressure of argon or nitrogen. The reaction vessels were stirred magnetically. Sensitive liquids and solutions were transferred via syringe and introduced into the reaction vessels through rubber septa.

Thin-layer chromatography was performed using Whatman precoated glass-backed silica gel plates. Visualization of the gels were effected by either ultraviolet illumination of exposure to iodine vapour. Column chromatography was performed using 230-400 mesh EM Science silica gel.

NMR spectra were measured using a Varian 500 spectrophotometer. NMR spectra were measured with deuterated chloroform, methanol or DMSO, as standard.

LC/Mass spectra were obtained on an Agilent 1100 series instrument equipped with a quaternary pump, a variable length detector and a C-18 column.

Example 3

To screen the effectiveness and ideal doses for the HAOC (Heteroaromatic organic compounds) of the present invention at blocking SYN aggregation two sets of assays can be utilized. The first set involves in vitro assays in cell free and cell based systems and the second includes in vivo studies in transgenic mouse models of PD.

In the present example the following HAOC, denominated as NPT200-5, was used:

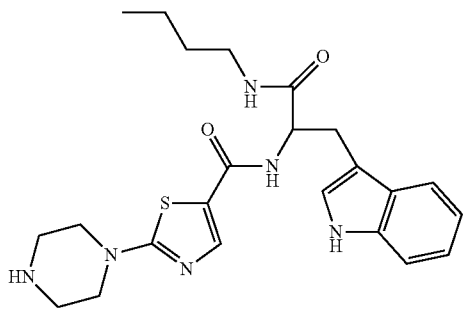 [SMILES: CCCCNC(=O)C(Cc1c[nH]c2ccccc12)NC(=O)c1cnc(N2CCNCC2)s1]

The objective is to identify with the in vitro assays a positive response by demonstrating a 50% effect on 2 out of the 3 assays at a 1 µM dose.

1. In Vitro Assays of SYN Aggregation and Toxicity

The in vitro studies include the following: i) effects on SYN oligomers in a cell free immunoblot assay of SYN aggregation; ii) effects on SYN accumulation and neurite outgrowth in neuronal cultures infected with a LV-SYN construct; and iii) effects on SYN oligomers in neuronal cultures infected with a LV-SYN construct.

For this purpose, recombinant SYN (1 µM, Calbiochem, USA) will be incubated at 37 and then at 56° C. for 16 hrs. After 1 hour of incubation the NPT200-5 and analogs will be added to the mix at concentrations ranging from 1 nM to 100 µM. Samples will be subjected to immunoblot analysis with the rabbit polyclonal SYN antibody (Millipore) and mouse monoclonal antibody against SYN (SYN211, 1:1000, Sigma) and analyzed in the VersaDoc imaging system using the Quantity One software (BioRad, Hercules, Calif., USA).

For the neuronal cell based assays, the neuroblastoma line B103 will be used. Cells will be infected with LV-SYN vector for 24 hrs, treated with the NPT200-5 at 0, 0.1, 1 and 10 µM for 24 hrs in serum free media. To infect the neural cells with LV vectors, multiples of infections (MOI) of 0.1, 1 or 5 (based on TU/ml on 293T cells) will be used. After 4-5 days in vitro, the % of transgene-expressing cells will be analyzed. The B103 cells will be maintained at 37° C., 5% $CO_2$ in Dulbecco's modified eagle medium (DMEM, high glucose) supplemented with 10% fetal bovine serum (Irvine Scientific, Irvine, Calif.) and 1% v/v penicillin/streptomycin. For analysis of SYN aggregation cell homogenates will be analyzed by immunoblot with antibodies against SYN and in coverslips by immunocytochemistry. For evaluation of neurite outgrowth coverslips will be immunostained with an antibody against MAP2 and analyzed with a digital Olympus microscope and the Image Quant System.

The LDH release assay (CytoTox 96 assay, Promega) will be performed to measure levels of toxicity (if any). Additional confirmation of cell viability will be obtained utilizing Hoechst staining and calcein AM/ethidium homodimer staining (Live/Dead assay, Molecular Probes). All assays will be performed in triplicate in 96-well plates according to the manufacturers' instructions.

2. In Vivo Studies in Transgenic Models of SYN Accumulation

Once a series of compounds are identified to be most active the next step will be to inject NPT200-5 and controls into our SYN transgenic (tg) mice, to test the in vivo effects. The first set of experiments will be daily injections for 2 weeks with compounds at 1, 10 and 100 nM. Blood, CSF, brain and liver will be analyzed for levels of SYN and compound. After preliminary data is obtained then more extensive studies with groups of 20 mice will be performed with daily injections in 3 and 6 month old mice for 3 and 6 months duration of treatment. Mice will be analyzed behaviorally, neuropathologically and biochemically for SYN aggregation and neurodegeneration. Blood and CSF will be analyzed for levels of SYN and NPT200-5 by mass spect and NMR. The compounds will be further refined and modified to increase permeability, access into the brain and bio-availability. The selected compounds will be first tested for toxicity in non tg mice. SYN knock out mice are viable and neurologically intact. This suggests that using a compound that blocks SYN will have low or no toxicity when tested in the SYN tg mice.

The lead compounds screened from these in vivo experiments will then be submitted for toxicological studies and prepared for a phase I clinical trial. The long term objective is to obtain funding and develop this compound for a phase II clinical trial in patients with PD.

The compounds of the present invention lead to a novel therapy for PD, LBD, AD and MSA based on blocking neurotoxic SYN oligomerization in the cell membrane.

Figure 1:
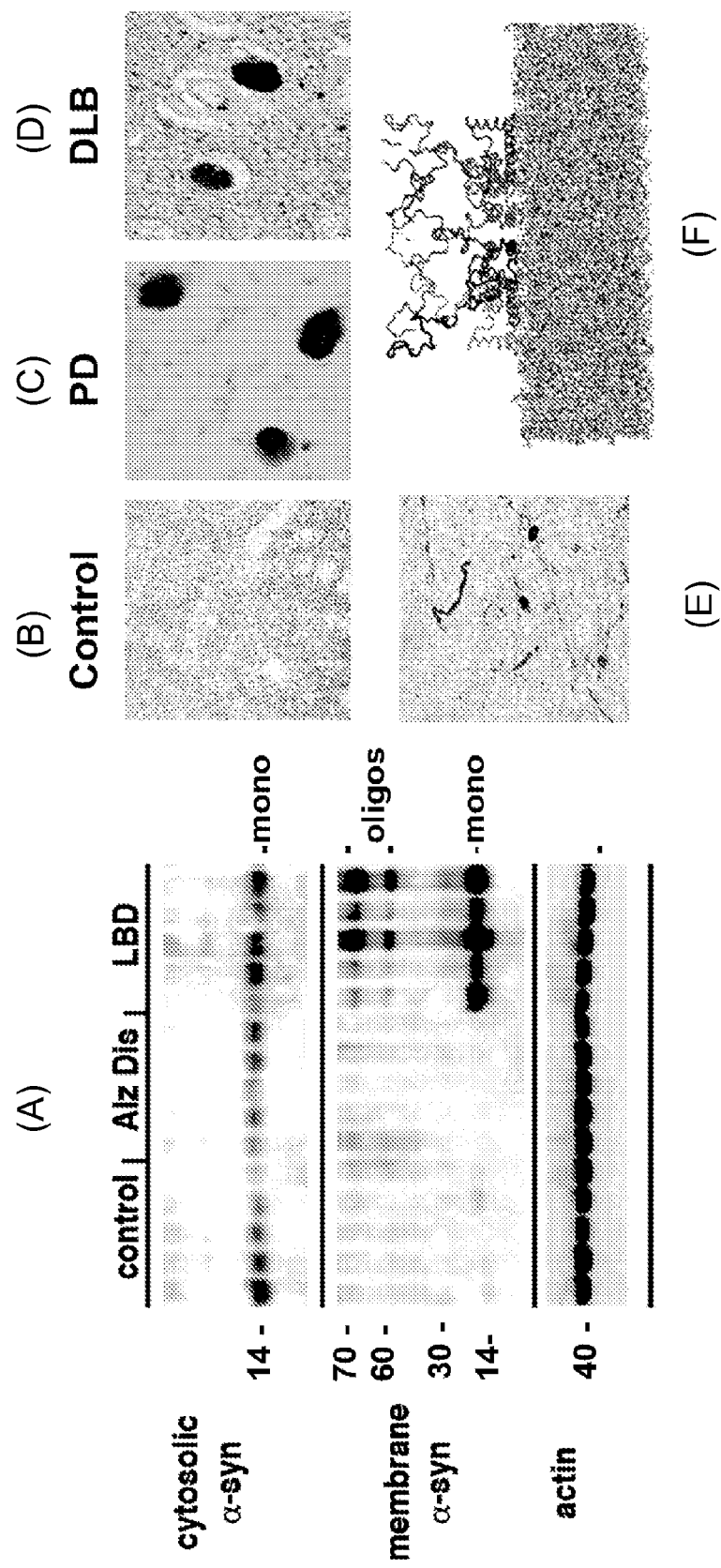
Figure 2:
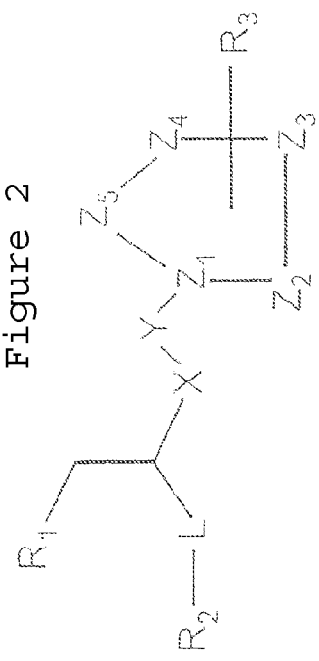
FIG. 2 shows chemical structure and synthesis of heteroaromatic organic compounds that inhibit synuclein.
Figure 2:
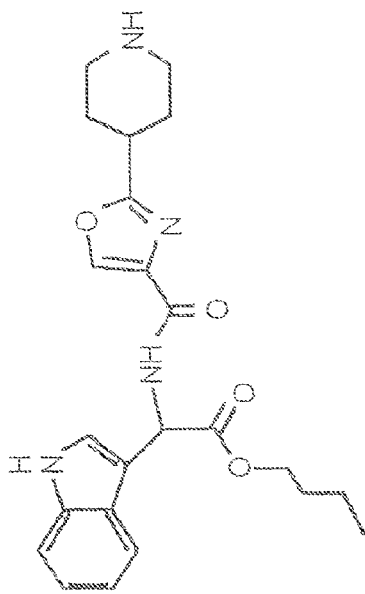
Figure 2:
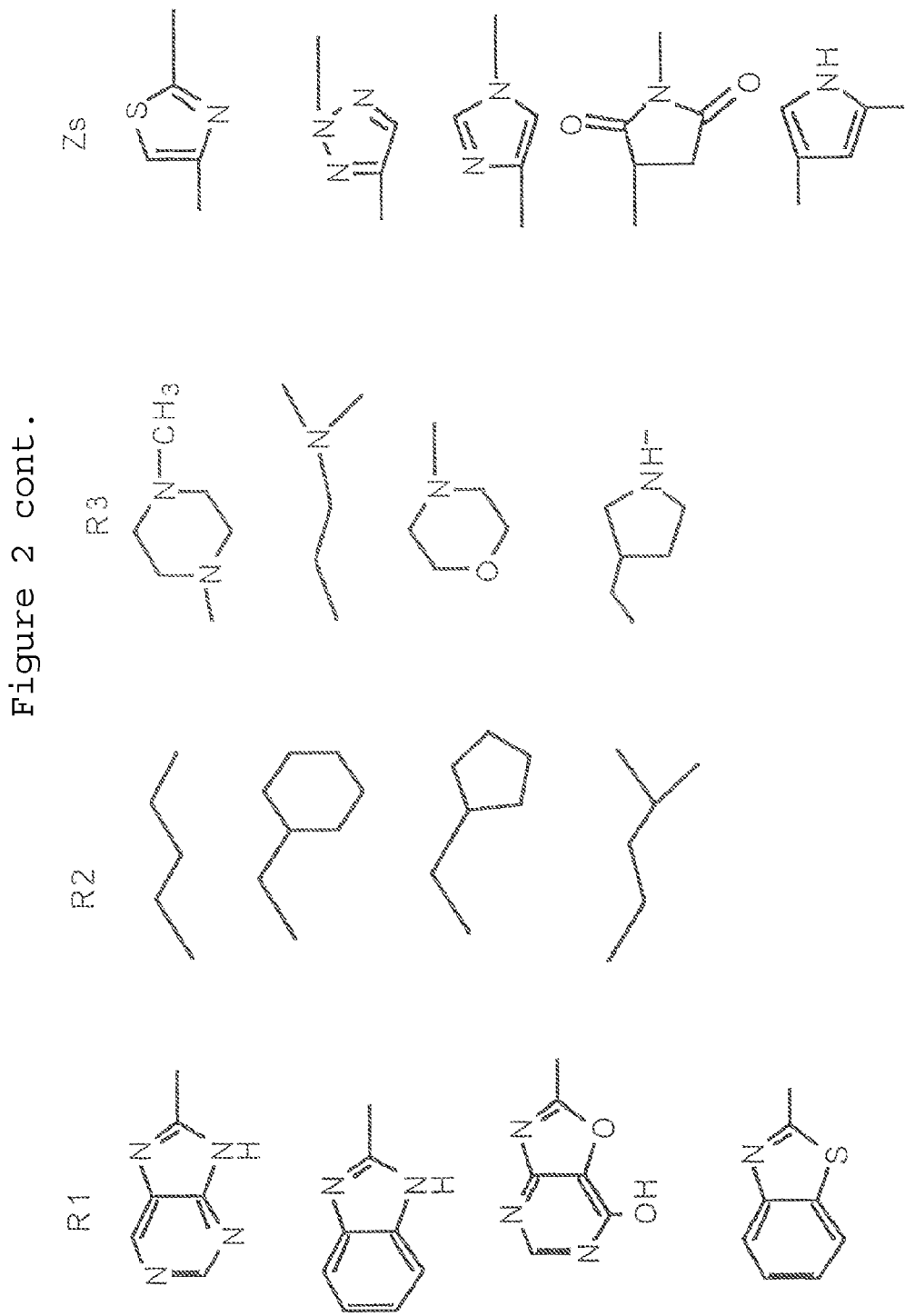
Figure 3:
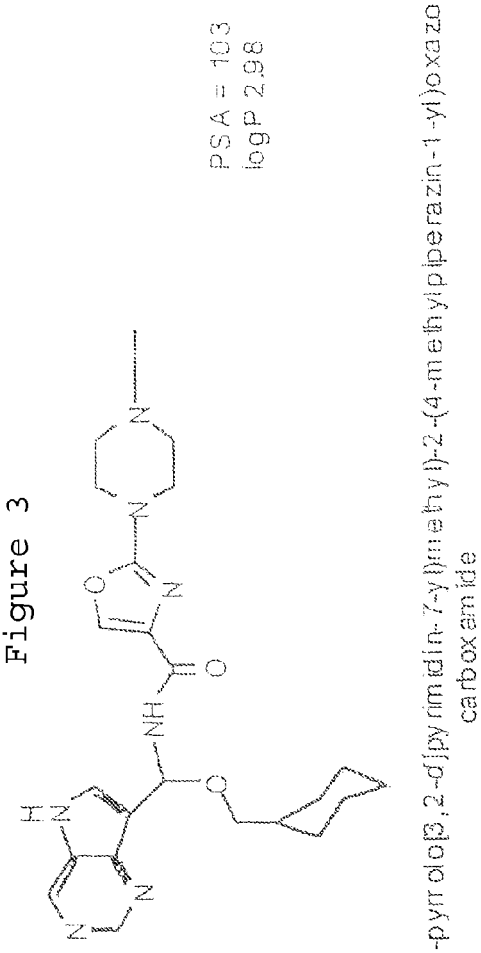
FIG. 3 shows examples of chemical compositions and formulas of heteroaromatic organic compounds that inhibit synuclein.
Figure 3:
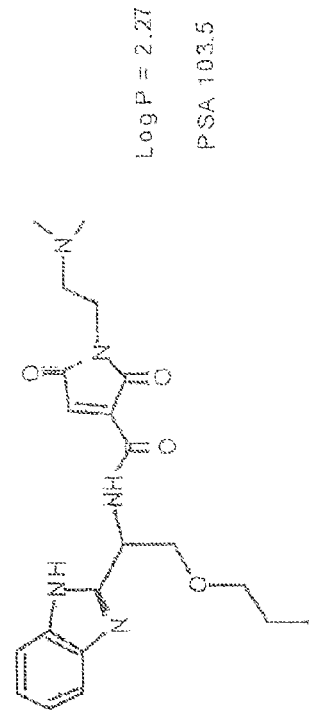
Figure 3:
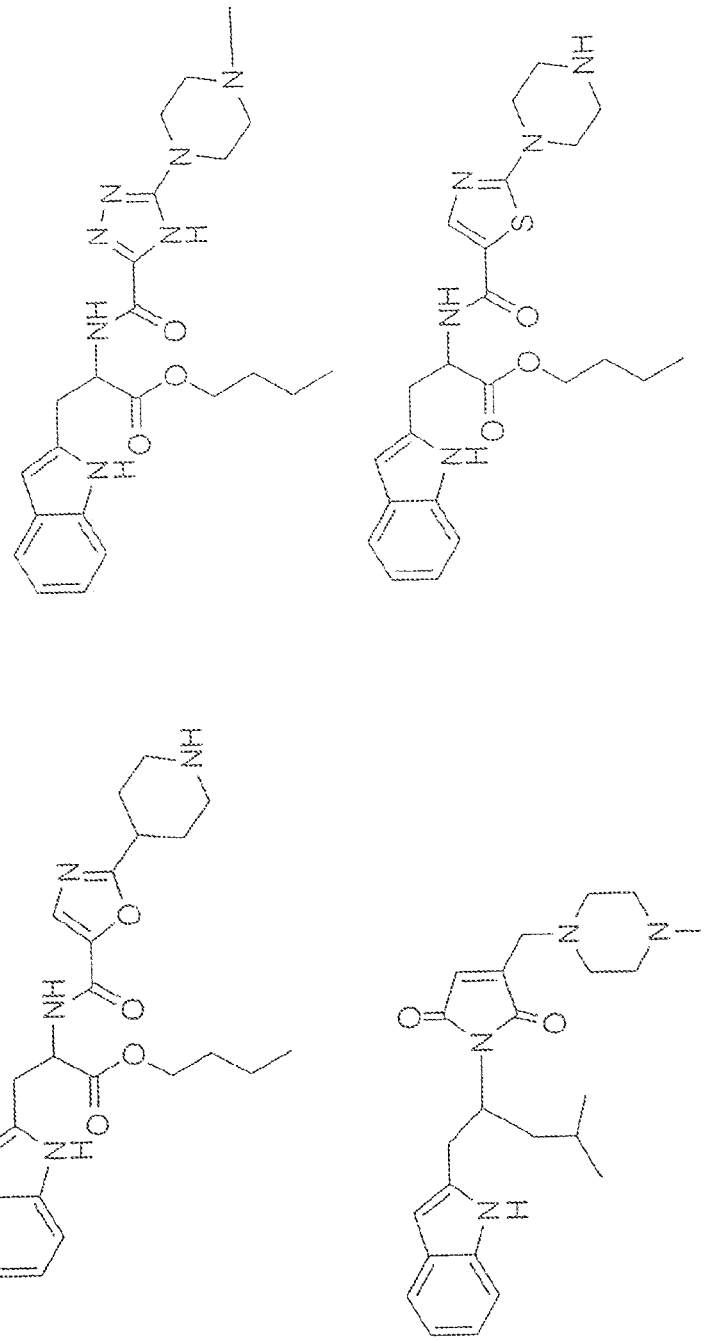
Figure 3:
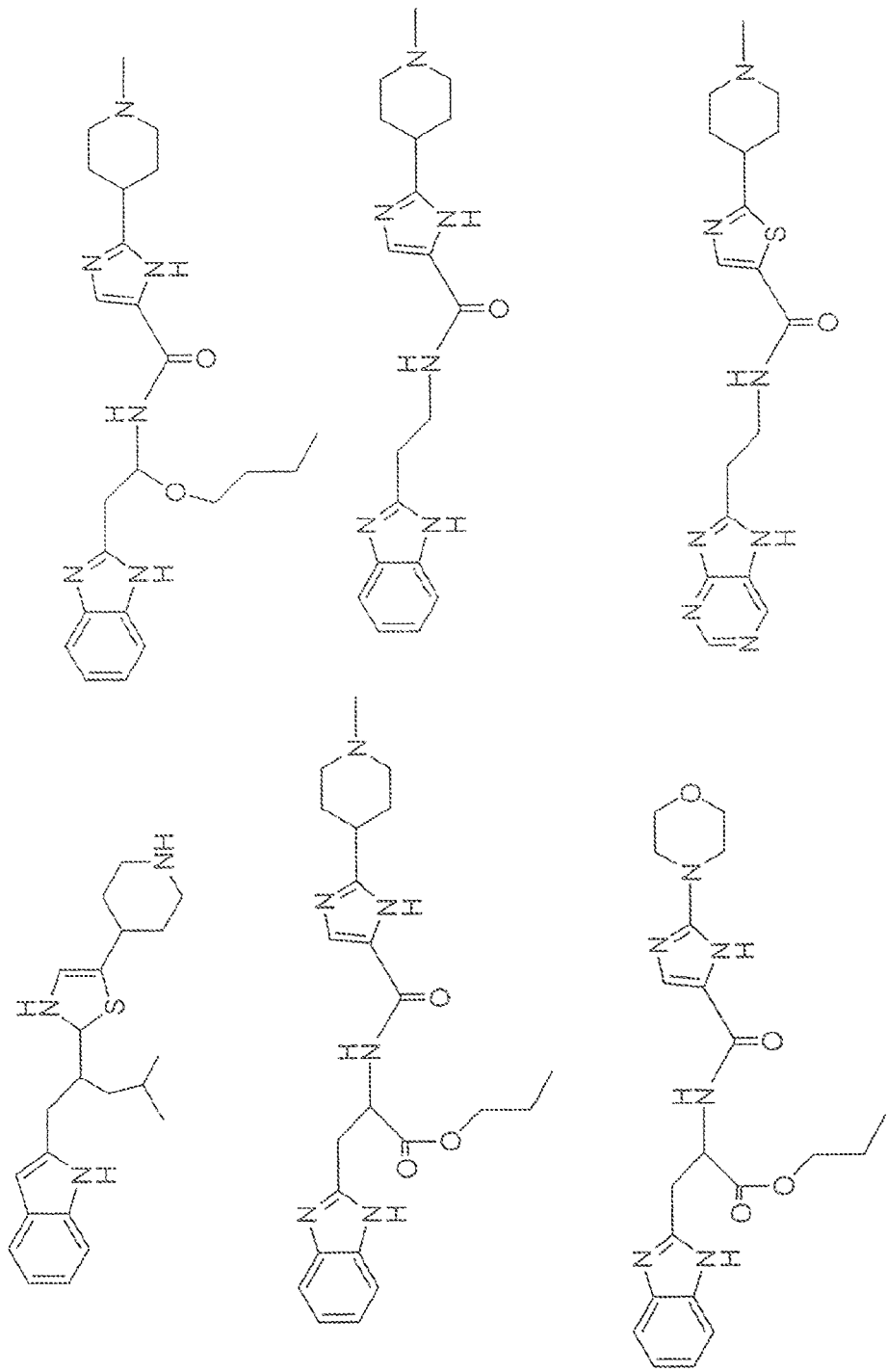
Figure 4:
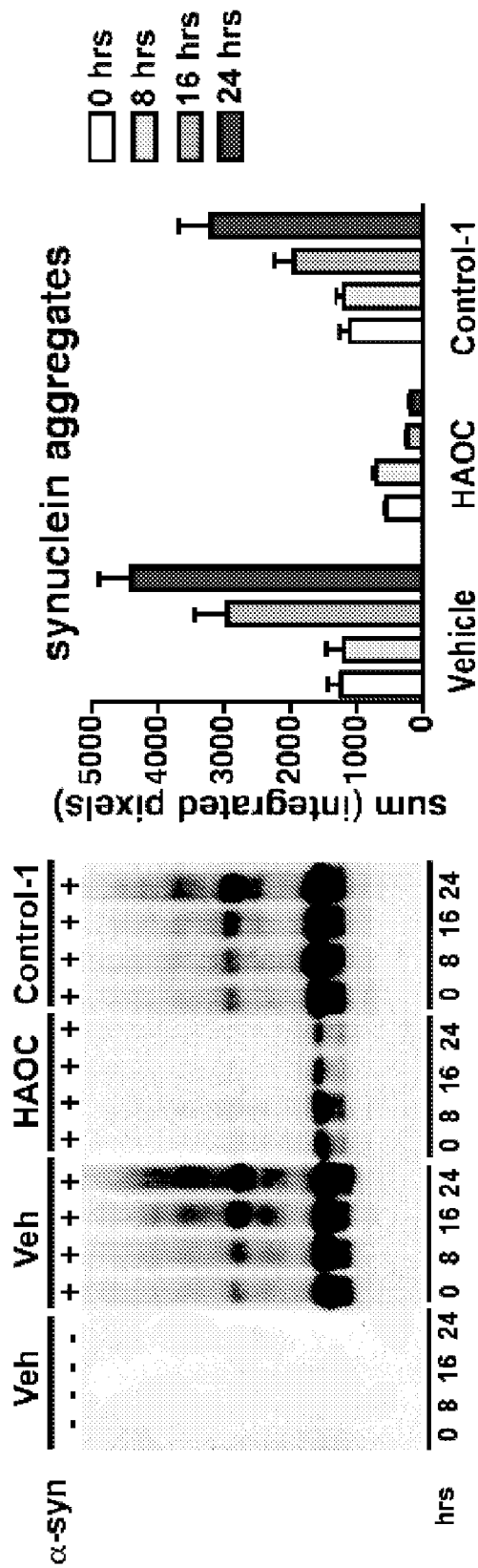
FIG. 4 shows cell free immunoblot analysis of the effects of the heteroaromatic organic compounds at blocking synuclein aggregation.

Computer simulations and calculations to pre-screen for the compounds that most likely might block SYN aggregation were performed. One (FIG. 4) of this heteroaromatic organic compounds with the appropriate controls was tested in a cell free system. For this purpose recombinant SYN (10 µM) was incubated at 37° C. for 0, 8, 16, and 24 hours with the peptides at 0, 0.1, 1 and 10 µM. Control experiments were performed with compounds that did not recognize the aggregated SYN molecules (control-1), with beta and gamma-synuclein as well as with a mutant SYN molecule that could not bind the peptide. The mixture was run in a gel, followed by immunoblot testing with SYN antibodies. This study showed that NPT200-5 (FIG. 2) was capable of completely blocking SYN aggregation at early and later time points of the oligomerization process (FIG. 4). For this assay SYN was used at 5 µM. The NPT200-5 reduced SYN aggregation by 50% at the 0.1 µM concentration.

Figure 5:
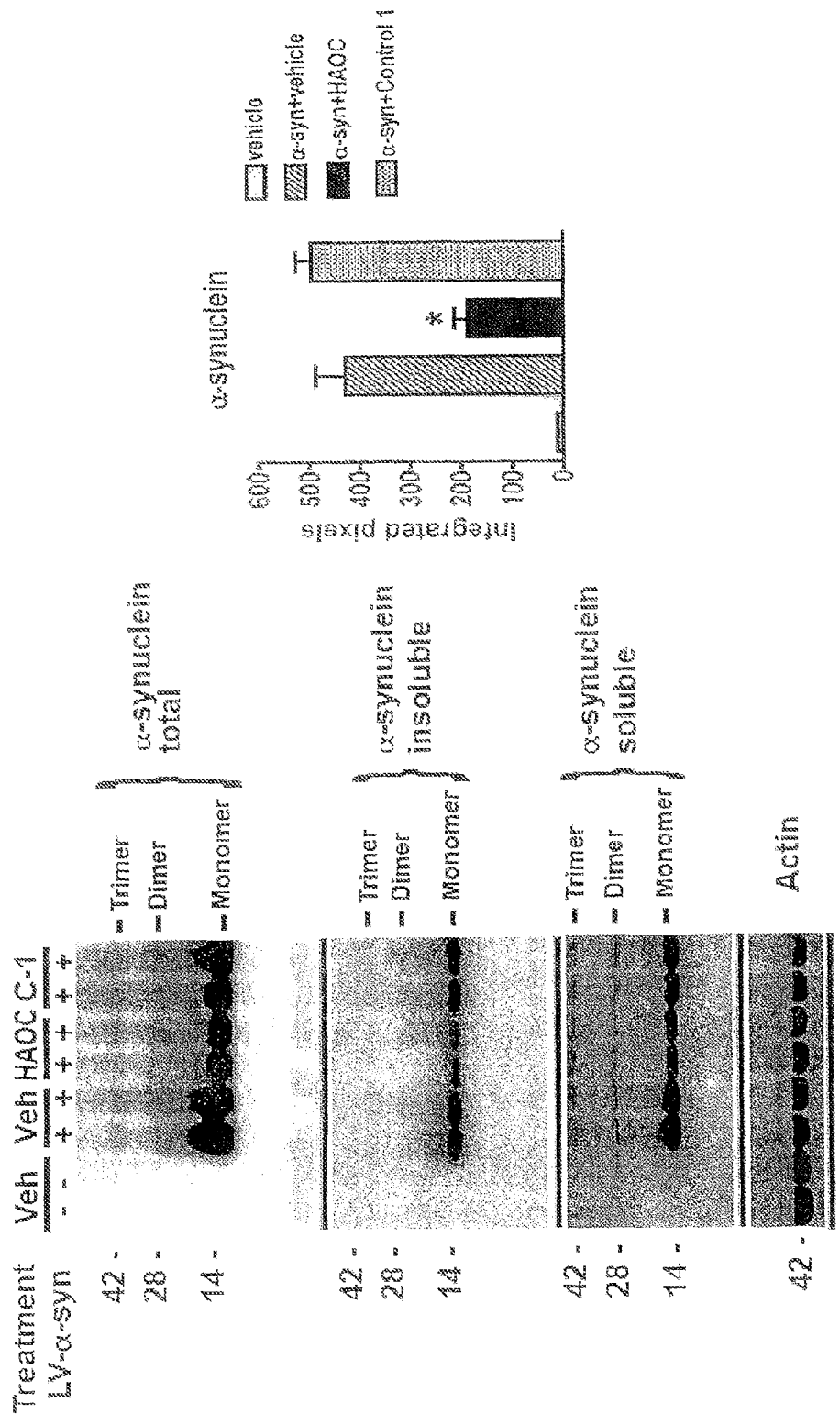
FIG. 5 shows immunoblot analysis of the effects of the heteroaromatic organic compounds at reducing alpha-synuclein aggregation in a neuronal cell based assay.

To test the activity of the NPT200-5 in vivo, the B103 neuronal cell line was infected with a lentivirus expressing SYN (wildtype) or empty vector (control) and cells expressing SYN were exposed to the NPT200-5 at 0, 0.1, 1 and 10 µM for 24 hrs. Cells were analyzed for SYN aggregation by immunoblot, confocal microscopy, neurite outgrowth and survival assays. By immunoblot, compared to controls, neuronal cells infected LV-SYN displayed the presence of high level expression of SYN monomer (14 kDa) as well as oligomers consistent with dimers, trimers and tetramers in the soluble and insoluble fractions (FIG. 5). After treatment with NPT200-5, there was a 50-60% reduction in the levels of aggregates (but also the monomers) in the various fractions (FIG. 5). Treatment with vehicle or with a control inactive compound had no effects in the levels of SYN. The NPT200-5 reduced SYN levels by 50% at the 0.1 µM concentration.

Figure 6:
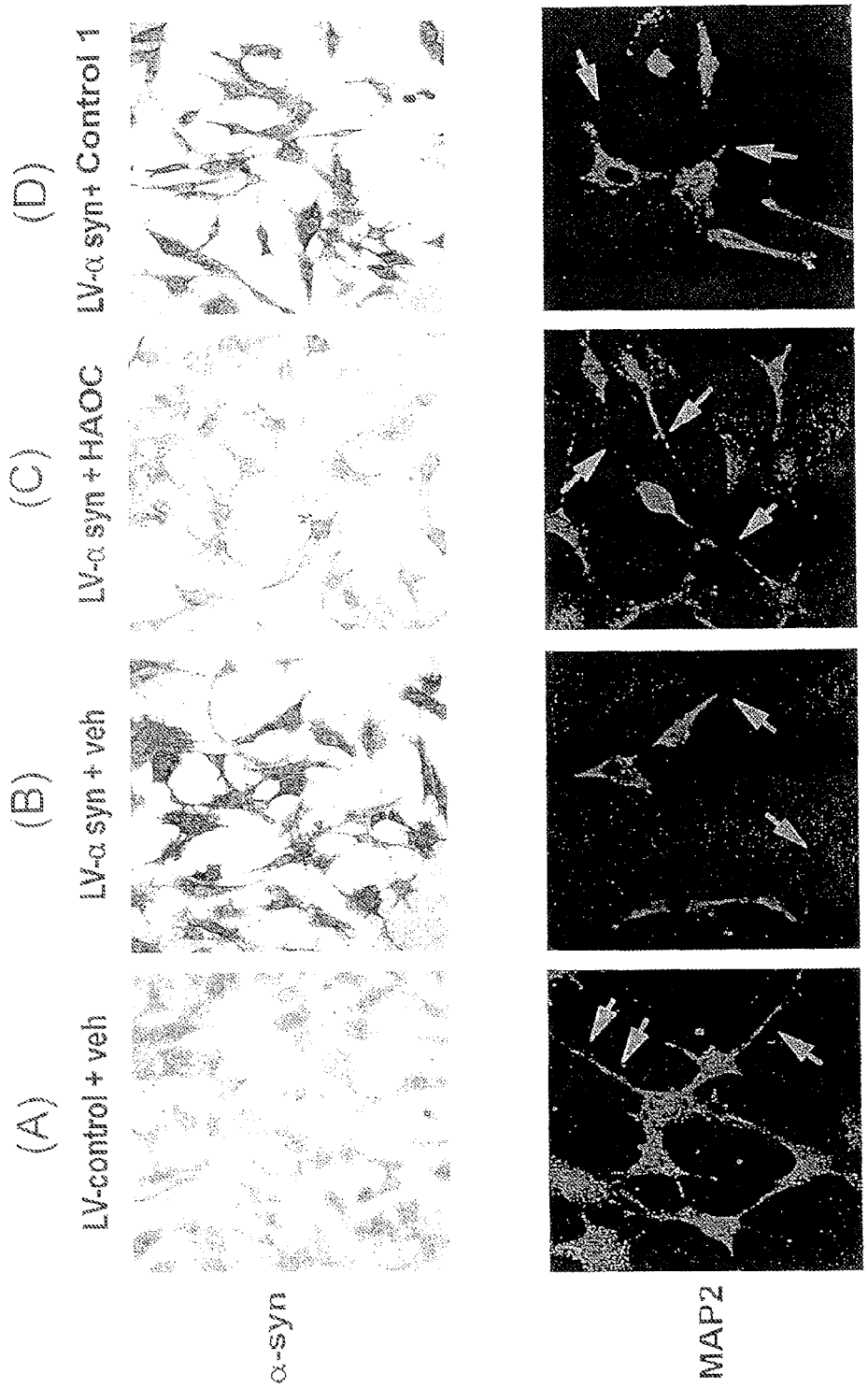
FIG. 6 shows confocal analysis of the effects of the heteroaromatic organic compounds at ameliorating neuronal pathology. (A-E) Analysis of levels of neuronal alpha-syn accumulation. (F-J) analysis of the neurite length and extension.
Figure 6:
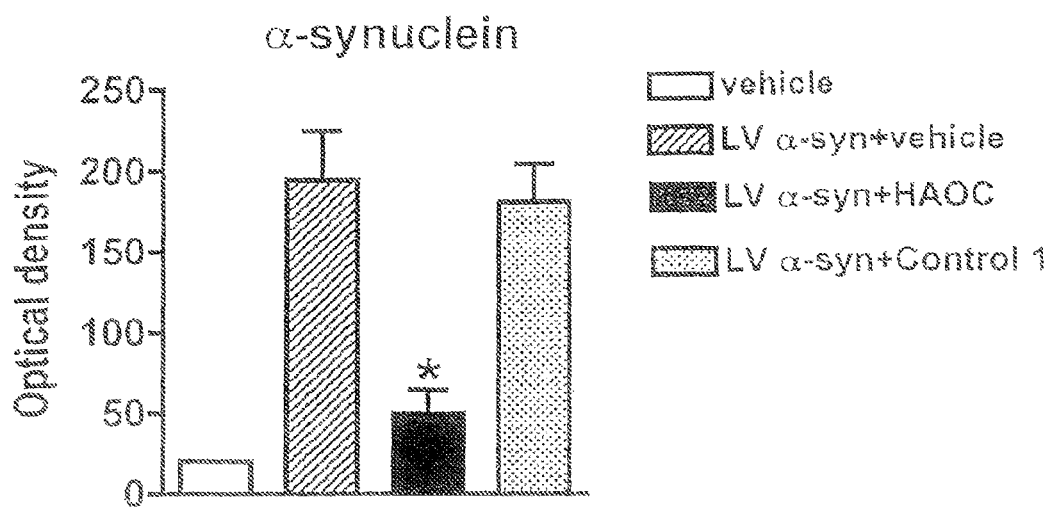
Figure 6:
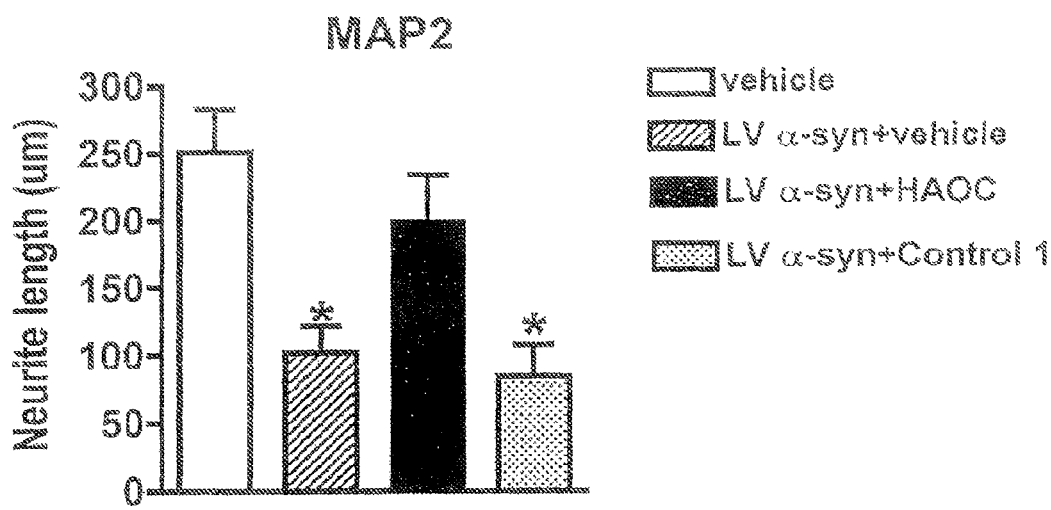

Similarly, neuronal cells were plated in coverslips, infected with LV-SYN vector for 24 hrs, treated with the NPT200-5 at 0, 0.1, 1 and 10 µM for 24 hrs in serum free media and analyzed by immunocytochemistry, confocal microscopy and image analysis. Compared to LV-empty vector control, neuronal cells infected LV-SYN showed high levels of SYN accumulation (similar to what may be observed in the brains of SYN tg mice and patients with PD) (FIG. 6). After treatment with NPT200-5, there was a 60-65% reduction in the levels of aggregates in the neuronal cell bodies and neurites (FIG. 6). Treatment with vehicle or with a control inactive compound had no effects on the levels of SYN. The NPT200-5 reduced SYN levels by 50% at the 0.1 µM concentration. Neuronal cells expressing high levels of SYN displayed reduced neurite outgrowth when analyzed with an antibody against the cytoskeletal protein MAP2. The NPT200-5 treatment (0.1 µM) ameliorated the deleterious effects on neurite length extension and improved cellular morphology (FIG. 6). Treatment with vehicle or with a control inactive compound had no protective effects.

Figure 7:
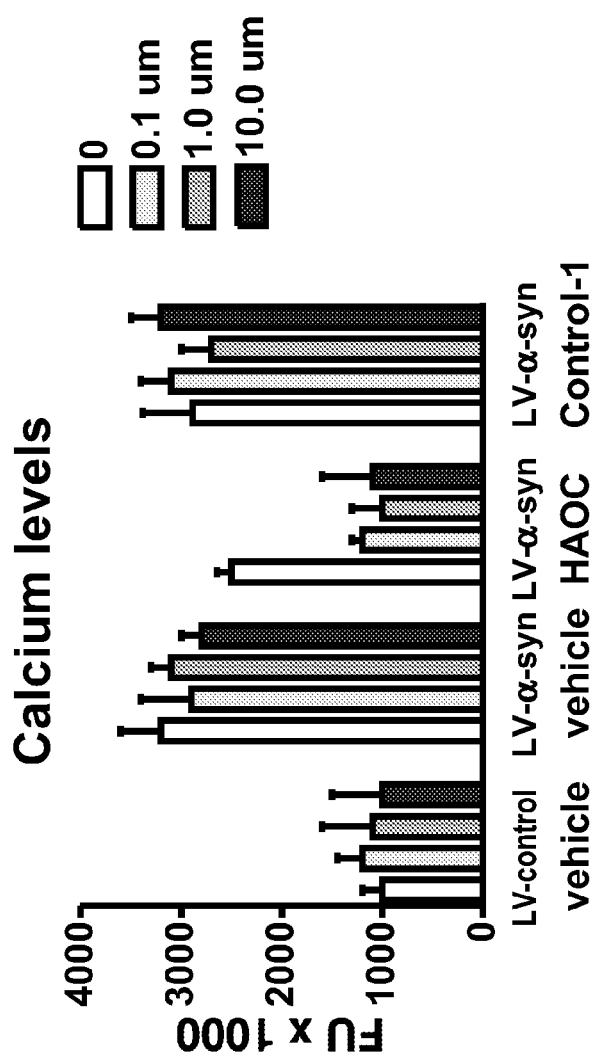
FIG. 7 shows an analysis of effects of the heteroaromatic organic compounds in calcium levels in neuronal cells expressing alpha-synuclein.

Next to ascertain the effects on neuronal activity, cells were infected with LV-SYN vector for 24 hrs, treated with the NPT200-5 at 0, 0.1, 1 and 10 µM for 24 hrs in serum free media, loaded with Flou-4 and analyzed by FLIPR assay to determine Ca++ levels. Compared to LV-empty vector control, neuronal cells infected LV-SYN showed 25-30% higher levels of Ca++ flow (FIG. 7). After treatment with NPT200-5, levels of Ca++ were back to baseline (FIG. 7). Treatment with vehicle or with a control inactive compound was unable to re-establish Ca++ levels. The NPT200-5 improved Ca++ levels by 50% at the 0.1 µM concentration. Finally, to examine the effects on neuronal survival, the MTT, LDH and BrDu assays were performed. This study showed no toxic effects of the NPT200-5 compounds at doses ranging from 0.1-10 µM (FIG. 7). All in vitro and cell based assays were repeated at least 4 times and experiments were performed blind.

The next step was to inject NPT200-5 and controls into SYN transgenic (tg) mice, to test the in vivo effects. The first set of experiments were daily injections for 2 weeks with compounds at 1, 10 and 100 nM. Blood, CSF, brain and liver were analyzed for levels of SYN and compound. After preliminary data had been obtained more extensive studies with groups of 20 mice were performed with daily injections in 3 and 6 month old mice for 3 and 6 months duration of treatment. Mice were analyzed behaviorally, neuropathologically and biochemically for SYN aggregation and neurodegeneration. Blood and CSF were analyzed for levels of SYN and NPT200-5 by mass spectrometer and NMR. The compounds were further refined and modified to increase permeability, access into the brain and bio-availability. The selected compounds were tested for toxicity in non tg mice. SYN knock out mice are viable and neurologically intact. This suggests that using a compound that blocks SYN will have low or no toxicity when tested in the SYN tg mice.

The invention claimed is:

1. A compound of formula (I):

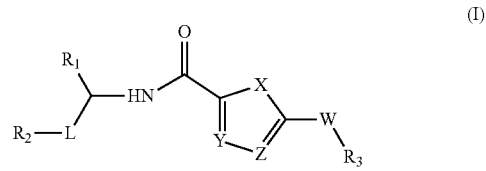

wherein
R$_1$ is selected from the group consisting of

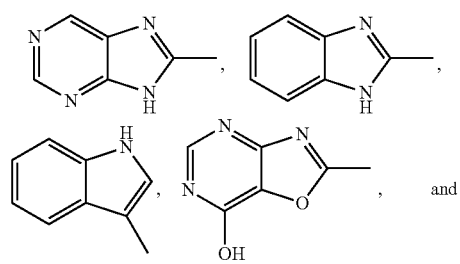

-continued

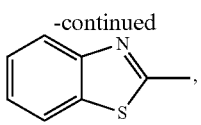

R₂ is an alkyl group with 1 to 18 carbon atoms or a substituted or unsubstituted cycloalkyl or aryl group,
R₃ is

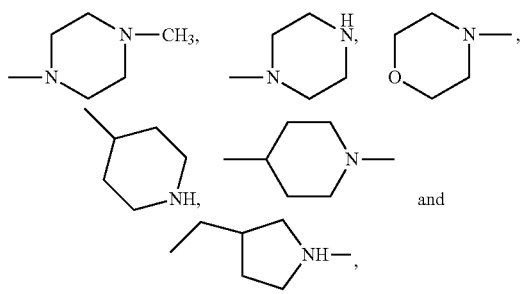

and

L is NHCO, O, S, NHCONH or NHCOO,
X, Y and Z are independently O, N, NH, S or CH,
W is a single bond or an alkyl group having from 1 to 6 carbon atoms,
or a pharmaceutically acceptable salt thereof or a pharmaceutically acceptable solvate of said compound or salt.

2. A compound selected from the group consisting of

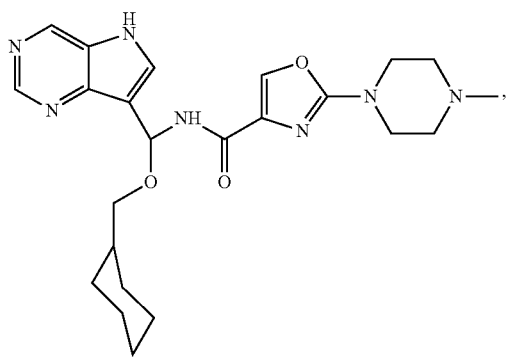

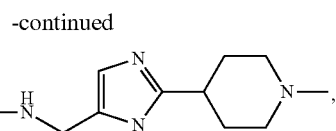

,

3. The compound according to claim 2, characterized in that the compound is

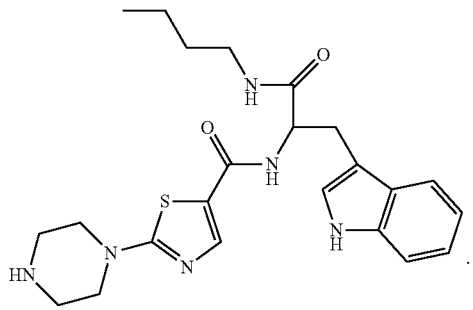 [SMILES: CCCCNC(=O)C(Cc1c[nH]c2ccccc12)NC(=O)c1cnc(N2CCNCC2)s1]

.

* * * * *